US 11,808,908 B2

(12) United States Patent
Guedes et al.

(10) Patent No.: US 11,808,908 B2
(45) Date of Patent: Nov. 7, 2023

(54) REAL-TIME RECONFIGURATION OF PHASED ARRAY OPERATION

(71) Applicant: Schlumberger Technology Corporation, Sugar Land, TX (US)

(72) Inventors: Orland Guedes, Clamart (FR); Mikhail Lemarenko, Beijing (CN); Hiroshi Hori, Clamart (FR); Jean-Baptiste Cozon, Clamart (FR); Beatriz Eugenia Otero Roldan, Sceaux (FR); Nicolas Fradin, Clamart (FR); Roel Van Os, Clamart (FR); Ram Sunder Kalyanraman, Richmond, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 139 days.

(21) Appl. No.: 17/169,861

(22) Filed: Feb. 8, 2021

(65) Prior Publication Data
US 2021/0247538 A1    Aug. 12, 2021

(30) Foreign Application Priority Data

Feb. 6, 2020    (EP) .................................... 20305113

(51) Int. Cl.
*G01V 1/50* (2006.01)
*E21B 47/00* (2012.01)
(Continued)

(52) U.S. Cl.
CPC .............. *G01V 1/50* (2013.01); *E21B 47/005* (2020.05); *E21B 47/006* (2020.05);
(Continued)

(58) Field of Classification Search
CPC ........ G01V 1/50; G01N 29/04; G01N 33/383; G01N 2291/0232; G01N 2291/0289;
(Continued)

(56) References Cited

U.S. PATENT DOCUMENTS 3,371,313 A    2/1968 Zemanek, Jr.
3,378,097 A    4/1968 Straus et al.
(Continued)

FOREIGN PATENT DOCUMENTS

EP    1348954 A1    10/2003
GB    2399411 A    9/2004

OTHER PUBLICATIONS

Zeroug et al., Sonic and Ultrasonic Measurement Applications for Cased Oil Wells, Aug. 2016, Insight, vol. 58, No. 8, pp. 423-430 (Year: 2016).*

(Continued)

*Primary Examiner* — Toan M Le
(74) *Attorney, Agent, or Firm* — Jeffrey D. Frantz

(57) ABSTRACT

Methods including determining a measurement plan, having acoustic measurements, and lowering in a borehole penetrating a subsurface formation a toolstring having phased array modules. Each phased array module includes acoustic transducers operable to emit an acoustic excitation signal and receive an echo signal, as well as a programmable circuit for setting one or more variables of the phased array module. The phased array modules are configured, including programming the programmable circuit to set variables of the phased array modules according to the measurement plan. The acoustic measurements of the measurement plan are performed using the configured phased array modules. One or more of the formation, a casing disposed in the borehole, (Continued)

and/or an annulus between the casing and the formation are characterized using results of the performed acoustic measurements.

20 Claims, 14 Drawing Sheets

(51) Int. Cl.
  *E21B 47/085* (2012.01)
  *E21B 47/005* (2012.01)
  *E21B 47/107* (2012.01)
  *E21B 47/002* (2012.01)
  *E21B 47/14* (2006.01)
  *E21B 49/00* (2006.01)
  *G01B 17/02* (2006.01)
  *G01N 29/04* (2006.01)
  *G01N 29/24* (2006.01)
  *G01N 33/38* (2006.01)
  *G01S 15/89* (2006.01)

(52) U.S. Cl.
  CPC ........ *E21B 47/0025* (2020.05); *E21B 47/085* (2020.05); *E21B 47/107* (2020.05); *E21B 47/14* (2013.01); *E21B 49/00* (2013.01); *G01B 17/02* (2013.01); *G01N 29/04* (2013.01); *G01N 29/2437* (2013.01); *G01N 33/383* (2013.01); *G01S 15/8945* (2013.01); *G01N 2291/0232* (2013.01); *G01N 2291/0289* (2013.01); *G01N 2291/044* (2013.01); *G01N 2291/106* (2013.01); *G01V 2210/1299* (2013.01); *G01V 2210/1429* (2013.01); *G01V 2210/60* (2013.01)

(58) Field of Classification Search
  CPC ..... G01N 2291/106; G01N 2210/1299; G01N 2210/1429; G01N 2210/60; G01S 15/8945; G01B 17/02; E21B 47/0025; E21B 47/005–006; E21B 47/0085; E21B 47/14; E21B 47/107; E21B 49/00
  See application file for complete search history.

(56) References Cited

U.S. PATENT DOCUMENTS

| | | |
|---|---|---|
| 3,524,162 A | 8/1970 | Zill |
| 4,255,798 A | 3/1981 | Havira |
| 4,594,691 A | 6/1986 | Kimball et al. |
| 4,641,724 A | 2/1987 | Chow et al. |
| 5,216,638 A | 6/1993 | Wright |
| 5,544,127 A | 8/1996 | Winkler |
| 6,483,777 B1 | 11/2002 | Zeroug |
| 6,614,716 B2 | 9/2003 | Plona et al. |
| 6,678,616 B1 | 1/2004 | Winkler et al. |
| 7,149,146 B2 | 12/2006 | Kuijk et al. |
| 7,219,762 B2 | 5/2007 | James et al. |
| 7,522,471 B2 | 4/2009 | Froelich et al. |
| 7,675,813 B2 | 3/2010 | Valero et al. |
| 7,689,362 B2 | 3/2010 | Froelich et al. |
| 7,913,806 B2 | 3/2011 | Pabon et al. |
| 9,534,487 B2 | 1/2017 | Zeroug et al. |
| 9,594,177 B2 | 3/2017 | Froelich et al. |
| 9,625,599 B2 | 4/2017 | Prioul et al. |
| 10,114,138 B2 | 10/2018 | Le Calvez et al. |
| 10,126,454 B2 | 11/2018 | D'Angelo et al. |
| 10,156,653 B2 | 12/2018 | Lemarenko et al. |
| 10,364,664 B2 | 7/2019 | Hori et al. |
| 2016/0216393 A1 | 7/2016 | Zhou et al. |
| 2017/0090057 A1 | 3/2017 | Thierry et al. |
| 2017/0168179 A1 | 6/2017 | Lemarenko et al. |
| 2018/0045844 A1 | 2/2018 | Oshima et al. |
| 2019/0017145 A1 | 1/2019 | Nelson et al. |
| 2020/0072999 A1 | 3/2020 | Pedrycz et al. |

OTHER PUBLICATIONS

Bellabarba, M. et al. "Ensuring Zonal Isolation Beyond the Life of the Well", Spring 2008 Oilfield Review, pp. 18-31, Schlumberger.

Ekstrom, M.P. "Dispersion Estimation from Borehole Acoustic Arrays Using a Modified Matrix Pencil Algorithm". 29th Asilomar Conference on Signals, Systems and Computer, vol. 2. Pacific Grove, California, Oct. 31, 1995.

Winkler, K. W. "Azimuthal velocity variations caused by borehole stress concentrations" Journal of Geophysical Research, vol. 101, No. B4, pp. 8615-8621, Apr. 10, 1996.

Lei, T., et al "Understanding Stress Effects on Borehole Acoustic Waves for Unconventional Shale Reservoirs". SPE-191404-MS. pp. 1-13, Sep. 24, 2018.

European_Search_Report_emailed_04Aug2020_for the equivalent Patent Application 20305113.1.

Communication Pursuant to Article 94(3) issued in European Patent Application No. 20305113.1 dated Apr. 11, 2023, 7 pages.

* cited by examiner

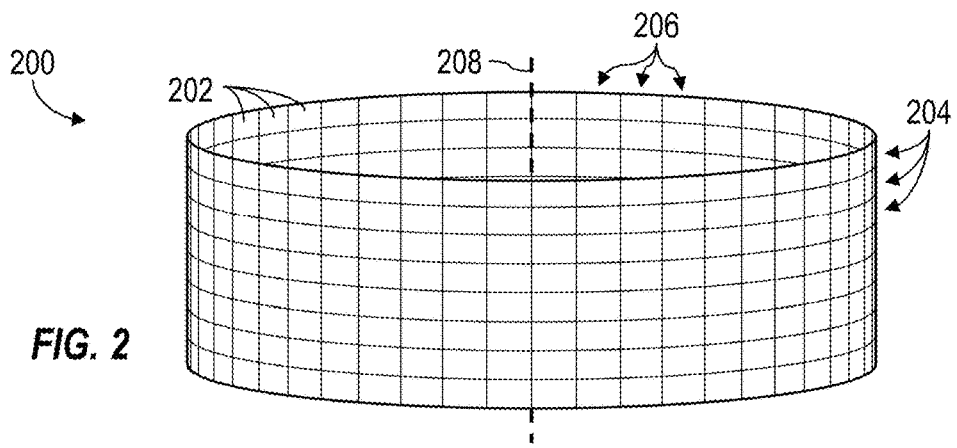
FIG. 2
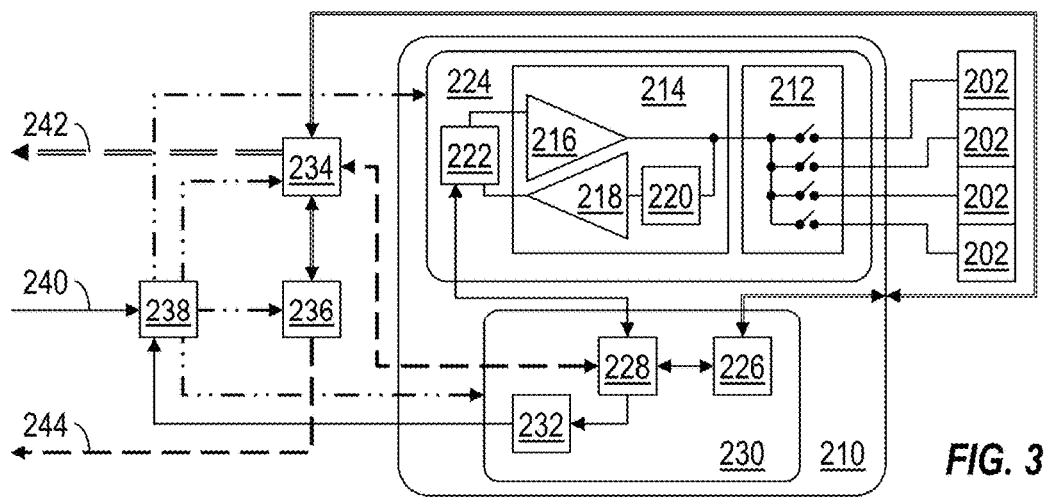
FIG. 3
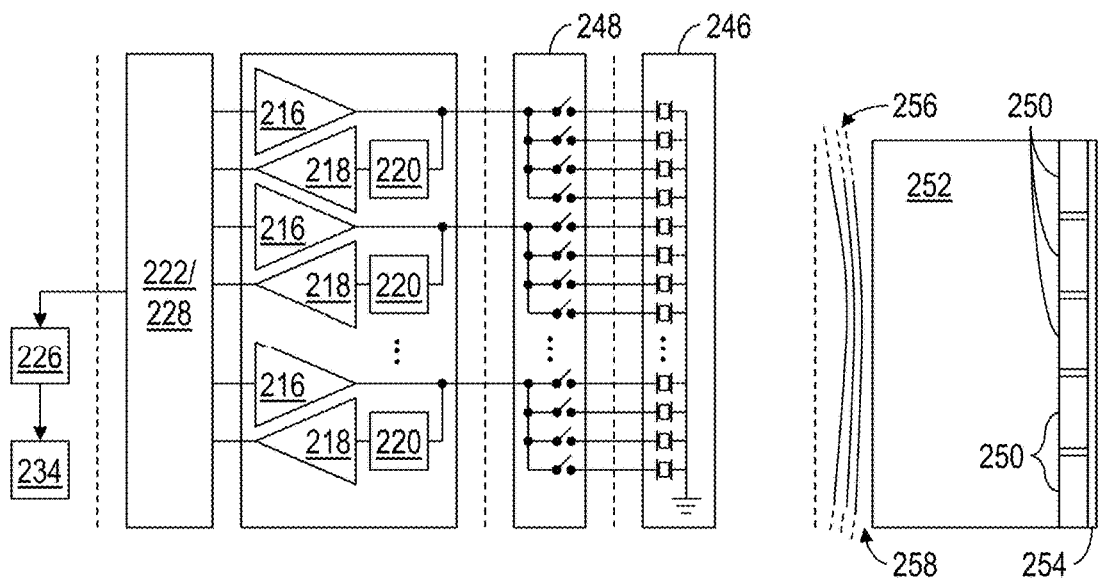
FIG. 4
FIG. 5

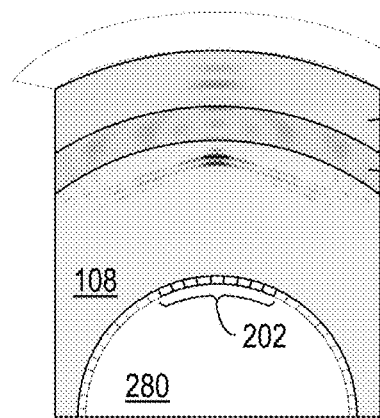 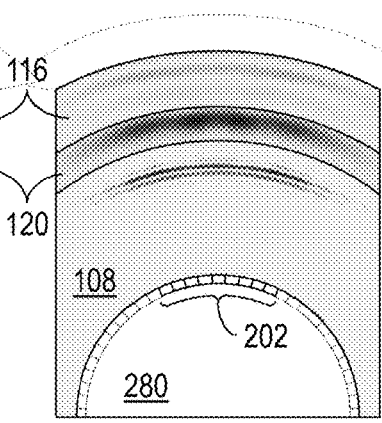 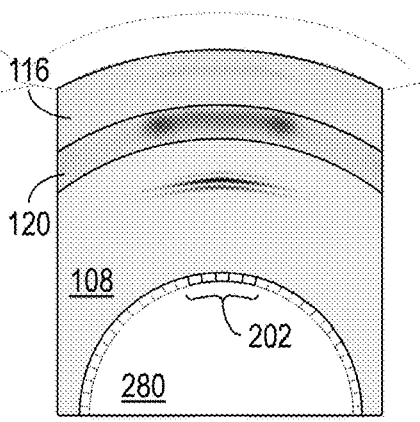
FIG. 39　　　　　FIG. 40　　　　　FIG. 41
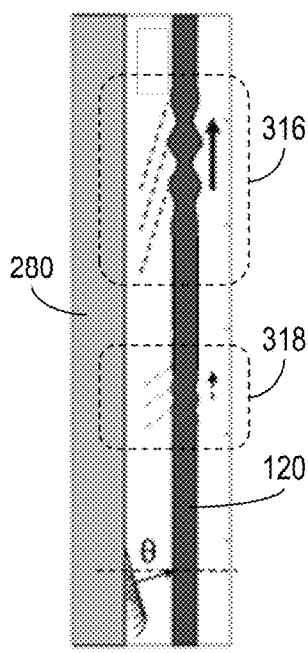
FIG. 42
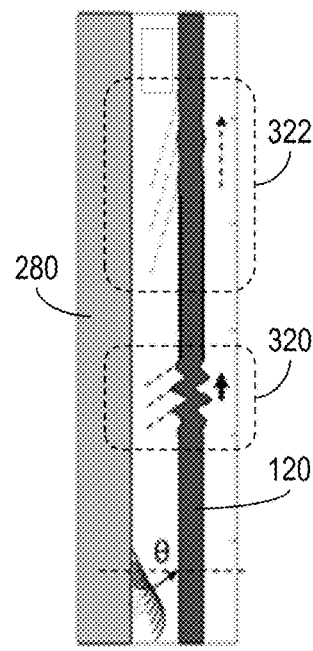
FIG. 43
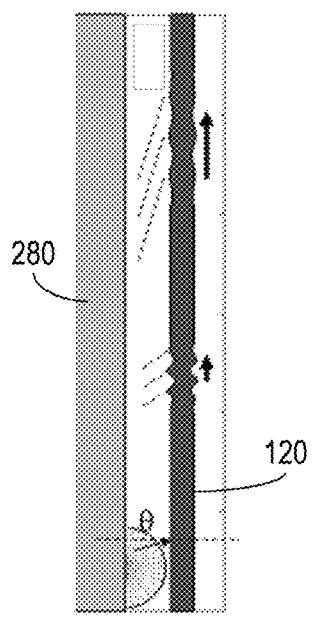
FIG. 44

REAL-TIME RECONFIGURATION OF PHASED ARRAY OPERATION

BACKGROUND OF THE DISCLOSURE

The present document is based on and claims priority to European Application No. 20305113.1, entitled "Real-Time Reconfiguration of Phased Array Operation" filed Feb. 6, 2020, which is incorporated herein by reference in its entirety.

Ultrasonic downhole imaging tools are used in oil and gas exploration and production (E&P) in both cased and uncased ("open") boreholes. For example, when utilized in cased boreholes, such ultrasonic imaging may be performed to inspect the casing and the cement securing the casing in the borehole to ensure well integrity. Defects in the casing, such as pit and holes and/or thickness reduction that are generated as a result of corrosion, and/or defects in well cement, such as fluid/gas-filled voids or localized acoustic/mechanical cement property changes, can be identified from anomalies in ultrasonic signals relative to the ones that are acquired in defect-less cemented casings. When utilized in open boreholes, ultrasonic imaging may be performed to visualize the borehole surface (ie formation) features, such as vugs, fractures, and/or textures and layerings (associated to acoustic properties) of the subterranean formation penetrated by the borehole, and to visualize borehole surface geometries, for both geological exploration and geophysics/geomechanics evaluation purposes.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method including determining a measurement plan having one or more acoustic measurements and lowering in a borehole penetrating a subsurface formation a toolstring having one or more phased array modules. Each phased array module includes acoustic transducers operable to emit an acoustic excitation signal and receive an echo signal, as well as a programmable circuit for setting one or more variables of the phased array modules. The method also includes configuring the one or more phased array modules, including programming the programmable circuit to set variables of the one or more phased array modules according to the measurement plan. The method also includes performing the one or more acoustic measurements of the measurement plan using the configured one or more phased array modules, and characterizing one or more of the formation, a casing disposed in the borehole, and/or an annulus between the casing and the formation, using results of the performed one or more acoustic measurements.

The present disclosure also introduces a system including a toolstring that includes one or more phased array modules and that is configurable for operation in a borehole that extends into a subsurface formation. Each phased array module includes acoustic transducer elements operable to emit an acoustic excitation signal and receive an echo signal, as well as a programmable circuit operable to set one or more variables relative to the one or more phased array modules. The toolstring is configurable to perform measurements using the one or more phased array modules. Each measurement corresponds to a different configuration by the programmable circuit of each phased array module. The system also includes a processing system to characterize one or more of the formation, a casing disposed in the borehole, and/or an annulus between the casing and the formation, using at least one measurement obtained via operation of one or more of the one or more phased array modules.

These and additional aspects of the present disclosure are set forth in the description that follows, and/or may be learned by a person having ordinary skill in the art by reading the material herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 2 is a perspective view of at least a portion of an example implementation of a phased array according to one or more aspects of the present disclosure.

FIG. 3 is a schematic view of at least a portion of an example implementation of a phased array system according to one or more aspects of the present disclosure.

FIG. 4 is a schematic view of another example implementation of the phased array system shown in FIG. 3.

FIG. 5 is a schematic view of a portion of the phased array system shown in one or both of FIGS. 3 and 4.

FIG. 39 is an axial view of a phased array measurement target and a phased array tool disposed in the target and emitting an ultrasonic beam in a focused mode according to one or more aspects of the present disclosure.

FIG. 40 is an axial view of a phased array measurement target and a phased array tool disposed in the target and emitting an ultrasonic beam in an unfocused mode according to one or more aspects of the present disclosure.

FIG. 41 is an axial view of a phased array measurement target and a phased array tool disposed in the target and emitting an ultrasonic beam in a mode between focused and unfocused according to one or more aspects of the present disclosure.

FIG. 42 is a side view of a phased array measurement target and a phased array tool disposed in the target for lower-angle, pitch-catch operation according to one or more aspects of the present disclosure.

FIG. 43 is a side view of a phased array measurement target and a phased array tool disposed in the target for higher-angle, pitch-catch operation according to one or more aspects of the present disclosure.

FIG. 44 is a side view of a phased array measurement target and a phased array tool disposed in the target for omni-angle, pitch-catch operation according to one or more aspects of the present disclosure.

DETAILED DESCRIPTION

Figure 1:
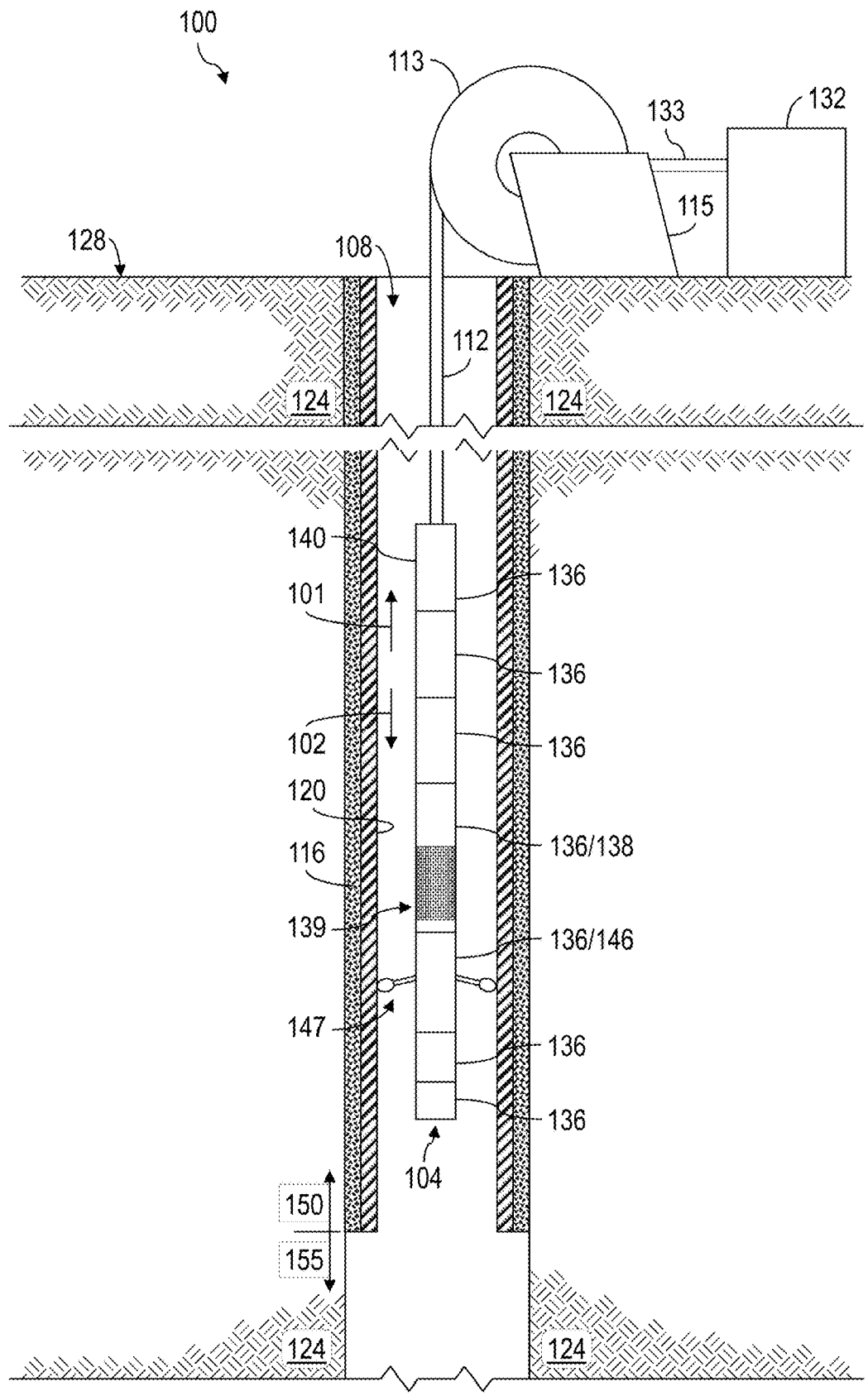
FIG. 1 is a schematic view of at least a portion of an example implementation of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity and does not in itself dictate a relationship between the various embodiments and/or configurations discussed. Moreover, the description of a first feature in contact with a second feature in the description that follows may include implementations in which the first and second features are in direct contact, and may also include implementations in which additional features may interpose the first and second features, such that the first and second features may not be in direct contact.

FIG. 1 is a schematic view of at least a portion of an example implementation of a wellsite system 100 to which one or more aspects of the present disclosure may be applicable. The wellsite system 100 may be onshore (as depicted) or offshore. In the example wellsite system 100 shown in FIG. 1, a toolstring 104 is conveyed in a borehole 108 via a wireline, slickline, and/or other conveyance means 112. The example wellsite system 100 may be utilized for evaluation of the borehole 108, cement 116 securing casing 120 within the borehole 108, a tubular (not shown) secured in the casing 120 (e.g., production services tubing), and/or a subterranean formation 124 penetrated by the borehole 108 in cased 150 or/and open hole 155 sections. The major part of the wellbore is shown as a "cased wellbore" but may be open hole (without cement or casing secured to the formation).

The toolstring 104 is suspended in the borehole 108 from the lower end of the conveyance means 112. The conveyance means 112 may be a single- or multi-conductor slickline or wireline logging cable spooled on a drum 113 of a winch 115 at the surface 128 of the wellsite from whence the borehole 108 extends. The wellsite surface 128 is the generally planar surface of the terrain (i.e., Earth's surface), a floor of a rig (not shown) at the wellsite, or other equipment at the wellsite, which is perpendicularly penetrated by the borehole 108. Operation of the winch 115 rotates the drum 113 to reel in the conveyance means 112 and thereby pull the toolstring 104 in an uphole direction 101 in the borehole 108, as well as to reel out the conveyance means 112 and thereby move the toolstring 104 in a downhole direction 102 in the borehole 108. The conveyance means 112 may include at least one or more conductors (not shown) that facilitates data communication between the toolstring 104 and surface equipment 132 disposed at the wellsite surface 128, including through one or more slip rings, cables, and/or other conductors (schematically depicted in FIG. 1 by reference number 133) electrically connecting the one or more conductors of the conveyance means 112 with the surface equipment 132. The conveyance means 112 may alternatively transport the tool string without a conductor inside the cable but with at least one module that can autonomously acquire and/or process and/or store downhole measurements in downhole memory without human intervention or communication with the surface equipment 132.

Although not illustrated as such in FIG. 1, the winch 115 may be disposed on a service vehicle or a stationary skid/platform. The service vehicle or stationary skid/platform may also contain at least a portion of the surface equipment 132.

The toolstring 104 comprises a plurality of modules 136, one or more of which may comprise an elongated housing and/or mandrel carrying various electronic and/or mechanical components. For example, at least one of the modules 136 may be or comprise at least a portion of a device for measuring a feature and/or characteristic of the borehole 108, the casing 120, a tubular installed in the casing 120 (not shown), the cement 116, and/or the formation 124, and/or a device for obtaining sidewall or inline core and/or fluid (liquid and/or gas) samples from the borehole 108 and/or formation 124. Other implementations of the downhole toolstring 104 within the scope of the present disclosure may include additional or fewer components or modules 136 relative to the example implementation depicted in FIG. 1.

The wellsite system 100 also includes a data processing system that may include at least a portion of one or more of the surface equipment 132, control devices and/or other electrical and/or mechanical devices in one or more of the modules 136 of the toolstring 104 (such as a downhole controller 140), a remote computer system (not shown), communication equipment, and/or other equipment. The data processing system may include one or more computer systems or devices and/or may be a distributed computer system. For example, collected data or information may be stored, distributed, communicated to a human wellsite operator, and/or processed locally (downhole or at surface) and/or remotely.

The data processing system may, whether individually or in combination with other system components, perform the methods and/or processes described below, or portions thereof. For example, the data processing system may include processor capability for collecting caliper, acoustic, ultrasonic, and/or other data related to the evaluation of the cement 116, the casing 120, a tubular installed in the casing 120 (not shown), and/or the formation 124, according to one or more aspects of the present disclosure. Methods and/or processes within the scope of the present disclosure may be implemented by one or more computer programs that run in a processor located, for example, in one or more modules 136 of the toolstring 104 and/or the surface equipment 132. Such programs may utilize data received from the downhole controller 140 and/or other modules 136 and may transmit control signals to operative elements of the toolstring 104, where such communication may be via one or more electrical or optical conductors of the conveyance means 112. The programs may be stored on a tangible, non-transitory, computer-usable storage medium associated with the one or more processors of the downhole controller 140, other modules 136 of the toolstring 104, and/or the surface equipment 132, or may be stored on an external, tangible, non-transitory, computer-usable storage medium that is electronically coupled to such processor(s). The storage medium may be one or more known or future-developed storage media, such as a magnetic disk, an optically readable disk, flash memory, or a computer-readable device of another kind, including a remote storage device coupled over one or more wired and/or wireless communication links, among other examples.

As designated in FIG. 1 by reference number 138, at least one of the modules 136 may be or comprise a phased array tool operable for acquiring acoustic measurements characterizing the borehole 108, the casing 120, a tubular installed in the casing 120 (not shown), the cement 116, and/or the formation 124. The phased array tool 138 comprises a phased array 139 of acoustic transducers that may each be operated as an acoustic transmitter and/or receiver. Example implementations of the phased array tool 138 within the scope of the present disclosure are described below. The one or more modules 136 may also include an orientation module permitting to map each measurement being oriented to the controlled azimuth of the tool 138 referring a tool face, to the azimuth of a borehole wall (casing or open hole surface) referring a geographical reference and/or gravitational orientation available from a well survey. Such module may include, for example, one or more of relative bearing (RB) or gravitational accelerometer, magnetometer and gyroscope sensors.

As designated in FIG. 1 by reference number 146, another one (or more) of the modules 136 may be or comprise a centralizer module. For example, the centralizer module 146 may comprise an electric motor driven by a controller (neither shown) and/or other means for actively extending ("opening") and retracting ("closing") a plurality of centralizing arms 147. Although only two centralizing arms 147 are depicted in the example implementation shown in FIG. 1, other implementations within the scope of the present disclosure may have more than two centralizing arms 147. Extension of the centralizing arms 147 aids in urging the phased array tool 138 to a central position within the casing 120, another tubular, or the borehole 108 being investigated by the phased array tool 138. Implementations of toolstrings within the scope of the present disclosure may include more than one instance of the phased array tool 138 and/or more than one instance of the centralizer module 146. The modules 136 may be conveyed in either or both of open hole 150 and cased hole 155 sections, including implementations in which the centralizer module 146 and the phased array module 138 may be configured or configurable for use in either or both of the two sections. The toolstring 104 may also be deprived of centralizer module 146.

FIG. 2 is a perspective view of at least a portion of an example implementation of a phased array 200 according to one or more aspects of the present disclosure. The phased array 200 shown in FIG. 2 is an example implementation of the phased array 139 shown in FIG. 1. Having a phased array downhole permits obtaining azimuthal measurements relative to the wellbore without rotation of the tool or a sensor of the tool.

The phased array 200 comprises acoustic transducer elements 202 arranged in eight rows 204 and 48 columns 206 extending around a central axis 208. However, implementations of the phased array 200 and other phased arrays within the scope of the present disclosure may include different numbers (including one) of rows 204 and/or columns 206. The phased array 200 may be configured such that the transducer elements 202 are collectively disposed azimuthally around a substantial portion (e.g., more than 50%) of the tool, perhaps the entire periphery of the tool.

FIG. 3 is a schematic diagram of at least a portion of an example implementation of acquisition electronics 210 that may be utilized with the phased array 200 shown in FIG. 2 according to one or more aspects of the present disclosure. The acquisition electronics 210 may comprise one or more multiplexers, switching devices, and/or other analog or digital means 212 for connecting to the individual transducer elements 202. A transmitter/receiver (TX/RX) front-end 214 may comprise one or more multi-channel transmitter (e.g., pulser) components 216 connected to the transducer connection means 212, one or more ultrasonic pulse reception components 218, and one or more TX/RX switches 220 connected between the transmitter component(s) 216 and the receiver component(s) 218. The transmitter component(s) 216 and receiver component(s) 218 are each connected to and operated by a control unit, such as a field-programable gate array (FPGA) 222, which may instead or additionally be or comprise a microprocessor unit (MPU), a microcontroller unit (MCU), a digital signal processing (DSP) component, and/or an application-specific integrated circuit (ASIC), among other examples. The transducer connection means 212 and control unit are part of a programmable circuit configurable to operate the phased array module in different manners in order to perform different measurements. The transducer connection means 212, the TX/RX front-end 214, and the FPGA 222 may be assembled on a dedicated circuit/subsystem board 224, among other configurations.

The acquisition electronics 210 may also comprise a digital signal processor (DSP) 226 connected to the FPGA 222, perhaps through another FPGA 228 dedicated to the DSP 226 or otherwise on the same circuit/subsystem board 230. The DSP board 230 may also comprise a digital-to-analog converter (DAC) 232. The components/functions of the two boards 224, 230 may also be combined in a single board or otherwise configured.

The memory and system controller boards serve for example to store the data and to communicate to surface and dump data once at surface. Each phased-array section should at least include the acquisition electronics. Memory and controller could be arranged elsewhere if the axial spacing requirements if the different array-section demand this. A separate master cartridge could for example house these functionalities.

The acquisition electronics 210 may also comprise or otherwise be associated with a memory circuit/subsystem board 234, a controller circuit/subsystem board 236, and a power supply circuit/subsystem board 238. The power supply board 238 is connected to and provides electrical power to each of the boards 224, 230, 234, 236, and may receive data and/or signals from at least one of the DAC 232, the acquisition board 210, and an external communication line 240. The memory board 234 may be connected to the DSP 226 and the controller board 236 for system control communication, to a data dump bus 242, and perhaps to the FPGA 228 (e.g., via a high-speed communication line) for communication to the board 224. The controller board 236 may also be connected to an external communication (e.g., high-speed) line 244.

FIG. 4 is a schematic diagram of at least a portion of an example implementation of the acquisition electronics 210 shown in FIG. 3 according to one or more aspects of the present disclosure. In FIG. 4, the transducer elements 202 are depicted by a set of capacitances 246. The switching connection means 212 are depicted by analog switches 248 that permit choosing which elements 202/246 to operate. The TX/RX front-end 214 is depicted by the TX/RX switches 220 isolating the high-voltage transmission pulse inputs 216 from the low-voltage receptors 218. For example, each receiver component 218 may comprise a low-noise amplifier (LNA), a programable-gain amplifier (PGA), one or more filter-stages, and an ADC. The FPGA 222/228 controls the circuitry to transmit and receive the pulses at requested delays. The FPGA 222/228 may also provide initial signal processing. For example, the FPGA 222/228 may comprise a serializer/deserializer (SERDES) block, providing correct beam forming. The DSP 226 may provide further processing to pre-compute answer products. The DSP 226 may send the data to the downhole memory 234 and send the data for direct uphole communication to the controller board 236. Some of the functionality may also be transferred to one or more application-specific integrated circuits (ASICs) (not shown), such as for setting gains and increasing the general operating envelope of the measurement system.

As schematically depicted in FIG. 5, the mechanical portion of the circumferential phased array 200 comprises piezoelectric elements 250, each forming a corresponding one of the transducer elements 202, and collectively sandwiched between a transmitter isolation (backing) 252 and a front face 254 protecting the piezo-electric elements 250 from the borehole environment. Through-wiring 256 may extend through a central passage 258 of the backing 252.

The piezoelectric elements 250 are arranged in a two-dimensional (2D) matrix extending around the circumference of the tool, as depicted in FIG. 2. Each element 202/250 has a thickness directly related to the frequency of operation of the array 200 as per standard piezoelectric application. A number of elements 202/250 can be operated at the same time, depending on the switching arrangement controlled via the acquisition electronics 210. The acquisition electronics 210 may be located downhole at a position near the piezoelectric elements 250 to acquire acoustic signals at favorable signal minimizing electrical noise that may be coupled via wiring and harness between the piezoelectric element 250 and the dedicated subsystem and circuit board 224.

Figure 6:
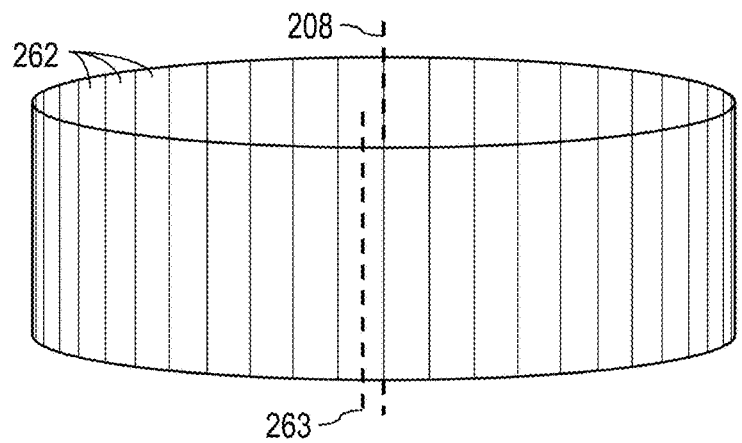
FIG. 6 is a perspective view of at least a portion of another example implementation of a phased array according to one or more aspects of the present disclosure.
Figure 7:
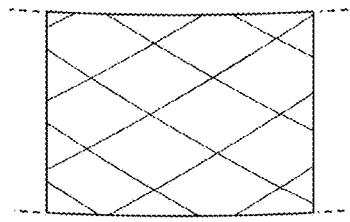
FIG. 7 is a perspective view of at least a portion of another example implementation of a phased array according to one or more aspects of the present disclosure.
Figure 8:
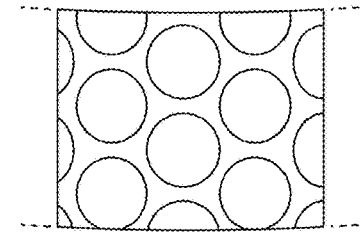
FIG. 8 is a perspective view of at least a portion of another example implementation of a phased array according to one or more aspects of the present disclosure.
Figure 9:
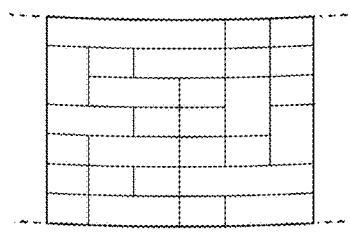
FIG. 9 is a perspective view of at least a portion of another example implementation of a phased array according to one or more aspects of the present disclosure.
Figure 10:
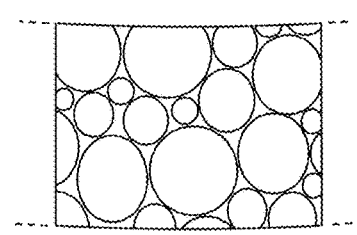
FIG. 10 is an axial view of a phased array measurement target and a phased array tool disposed in the target and emitting an ultrasonic beam with a linear wavefront having a zero-degree steering angle according to one or more aspects of the present disclosure.

The transducer elements 202 may be arranged in configurations other than the 2D matrix depicted in FIG. 2. For example, FIG. 6 depicts a one-dimensional (1D) matrix having a single row of elements 262, each of which may be substantially rectangular having a major axis 263 extending parallel to the central axis 208. However, the 1D matrix elements 262 may also be substantially square (similar to the elements 202 depicted in FIG. 2) or otherwise shaped. The transducer elements 202 may instead be arranged as a paved array, as depicted by the example implementations shown in FIGS. 7 and 8. The transducer elements 202 may instead be arranged in arbitrary configurations, as depicted by the example implementations shown in FIGS. 9 and 10. Moreover, while FIGS. 2 and 6-10 depict rectangular and circular transducer elements, the transducer elements may have polygonal and/or other shapes. The axial length of the phased array may also vary within the scope of the present application. Arbitrary configurations may also generate incoherent noise statistics, such that transducer-induced noise may inherently be reduced.

Figure 11:
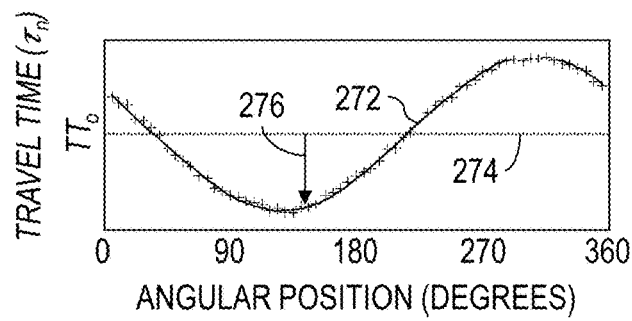
FIG. 11 is graph pertaining to one or more aspects according to one or more aspects of the present disclosure.
Figure 12:
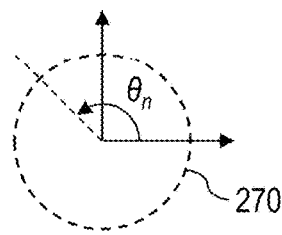
FIG. 12 is a schematic view related to the graph shown in FIG. 11.

As mentioned above, a phased array may provide different measurements, permitting characterization of different wellbore or tool parameters. Eccentricity of a phased array within the scope of the present disclosure can be determined from travel-time measurements of a particular operational mode of the tool, including, for example, firing each or a substantial number (e.g., more than 50%) of azimuthally distributed transducers of at least one row of the phased array and receiving the reflected waveform on all transducers. For example, FIG. 11 is a graph of example measurements of travel-time $\tau_n$ (denoted by "+" symbols) versus angular position $\theta_n$ of a number N of transducer elements of a phased array, such as the example phased array 270 schematically depicted shown in FIG. 12. The angular position $\theta_n$ may be equi-spaced, but may instead be arbitrary spaced. In FIG. 11, a sinusoidal curve 272 represents a fitting (e.g., via regression) of the $\tau_n$ measurements, line 274 represents an average $TT_o$ of the $\tau_n$ measurements, and arrow 276 represents $\delta_n$, the two-way delay from the average $TT_o$ at the $n^{th}$ element. The average 274 may be determined utilizing Equation (1) set forth below, although statistical methods may also be utilized, such as median or mode.

$$TT_o = \frac{1}{N}\sum_{n=1}^{N}\tau_n \quad (1)$$

The two-way delay $\delta_n$ may be determined utilizing Equations (2)-(6) set forth below.

$$\delta_n = a \cdot s_n + b \cdot c_n \quad (2)$$

$$s_n = \sin\theta_n \quad (3)$$

$$c_n = \cos\theta_n \quad (4)$$

$$a = \frac{\sum_{n=1}^{N}(\tau_n \cdot s_n)}{\sum_{n=1}^{N}(s_n)^2} = \frac{1}{N}\sum_{n=1}^{N}(\tau_n \cdot s_n) \quad (5)$$

$$b = \frac{\sum_{n=1}^{N}(\tau_n \cdot c_n)}{\sum_{n=1}^{N}(c_n)^2} = \frac{1}{N}\sum_{n=1}^{N}(\tau_n \cdot c_n) \quad (6)$$

The coefficients a and b may be used to determine the eccentering orientation through a simple arctangent or other methods known to those skilled in the art. After the eccentricity is determined, new variables, such as time-delays, may be set for the phased array module, such as for phasing of the beam (for the following measurement) and/or to ensure that the emitted wave is no longer perpendicular to the tool but is slightly steered such that it is perpendicular to the target. This may aid in ensuring that the same elements that fire also receive the maximum energy.

Different measurements may be taken with the phased array, such as pulse-echo measurements in which the acoustic excitation pulse is directed substantially normal to the borehole wall (such as the inner wall of the casing in a cased hole implementation, or the formation in an open hole implementation) or pitch-catch measurements in which the acoustic excitation pulse is directed so as to reach the borehole wall at a non-zero incidence angle relative to an axis normal to the borehole wall.

The phased arrays within the scope of the present disclosure may be operated in different operational modes, each generating a different wavefront profile, as depicted in FIGS. 13-18, in which a phased array tool 280 comprises a phased array of transducer elements 282 (only a few of which are shown) is disposed in a casing or other target 284. Delays can be applied to the firing elements 282 such that an ultrasonic beam can be directed to an intended one of various orientations utilizing one of various shaped wavefronts 286, 288, 290, 292, 294. Each firing element behaves as a point source and excites a circular wave of a different diameter depending on the respective delay. The lower-most firing element 297 provides a circular wavefront 299 of different diameters depicted in FIGS. 13-17 as examples.

Figure 13:
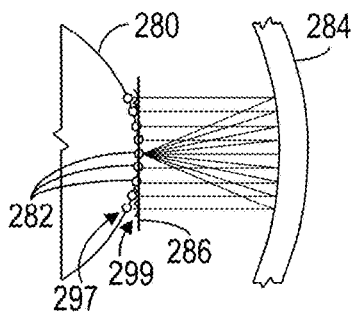
FIG. 13 is an axial view of a phased array measurement target and a phased array tool disposed in the target and emitting an ultrasonic beam with a linear wavefront at a zero-degree steering angle according to one or more aspects of the present disclosure.
Figure 14:
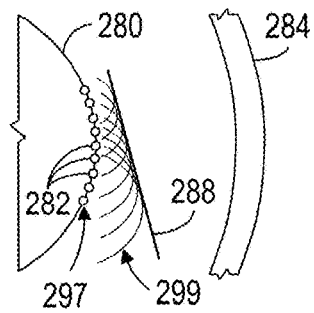
FIG. 14 is an axial view of a phased array measurement target and a phased array tool disposed in the target and emitting an ultrasonic beam with a linear wavefront having a low steering angle according to one or more aspects of the present disclosure.
Figure 15:
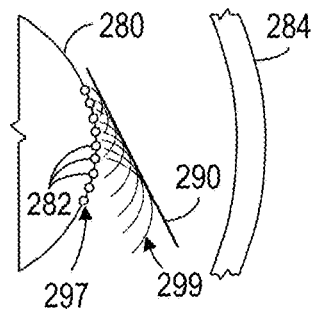
FIG. 15 is an axial view of a phased array measurement target and a phased array tool disposed in the target and emitting an ultrasonic beam with a linear wavefront having a high steering angle according to one or more aspects of the present disclosure.
Figure 16:
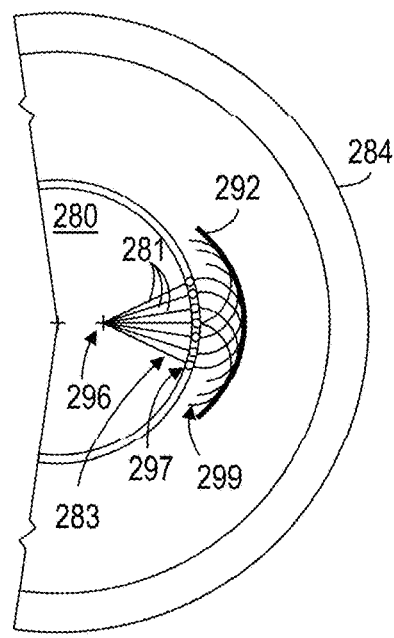
FIG. 16 is an axial view of a phased array measurement target and a phased array tool disposed in the target and emitting an ultrasonic beam with an unfocused circular wavefront having a geometric center inside the target and a radius less than the radius of the phased array tool according to one or more aspects of the present disclosure.
Figure 17:
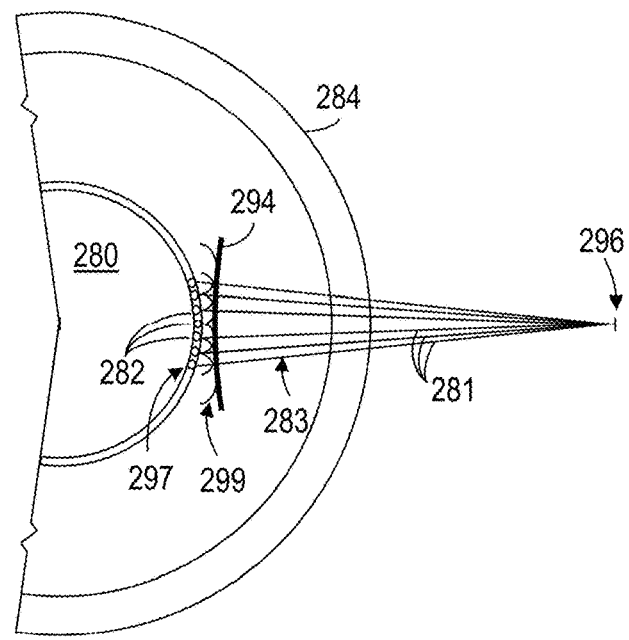
FIG. 17 is an axial view of a phased array measurement target and a phased array tool disposed in the target and emitting an ultrasonic beam with a focused circular wavefront having a geometric center outside the target and a radius greater than the radius of the phased array tool according to one or more aspects of the present disclosure.

Delay time may be determined in a way that the circular wavefronts of individual firing elements 282 form a linear wavefront profile following Huygens principle in an azimuthal steering mode. For example, with regard to azimuthal steering, FIG. 13 depicts a line wavefront 286 at a zero-degree steering angle, in which the echo from the target 284 is geometrically focused at the central one of the elements 282. Similarly, FIG. 14 depicts a line wavefront 288 with a low steering angle relative to the +X axis (horizontal axis relative to the page), and FIG. 15 depicts a line wavefront 290 with a high steering angle relative to the +X axis. FIG. 16 depicts an azimuthally unfocused mode where an unfocused, circular wavefront 292, corresponding to a circular convex wavefront profile, i.e., that is not directed toward a specific point in the subterranean formation, is emitted by the phased array tool 280, and FIG. 17 depicts an azimuthally focused mode where a focused, circular wavefront 294, corresponding to a circular concave wavefront profile, i.e., that is directed toward a specific point 296 in the subterranean formation, is emitted by the phased array tool 280.

In the focused mode, the delays of the transducers 282 may be determined so that the specific focusing point 296 is located in any appropriate location, such as on the borehole wall (including the formation or the casing inner wall), casing outer wall, in the annulus between the tool 280 and the casing/formation, or in a specific zone of the formation. The focused mode may generate a measurement with high resolution, focused on the feature of interest. Focused and unfocused circular wavefronts can be generated by setting the geometric center 296 of the circular wavefront inside (FIG. 16) or outside (FIG. 17) the phased array tool 280.

The wavefronts depicted in FIGS. 13-17 are merely examples. Other steering angles and geometric wavefront shapes, which can be generated by various combinations of delays and numbers of firing elements for the emission, are also within the scope of the present disclosure. This azimuthal wavefront control can be also combinable or simultaneously achieved with the axial steering and wavefront shape control described below.

The following description provides additional details regarding the configuration of the one or more phased arrays and the variables that may be set during the configuration operation. That is, the relative delays applied to the transducers in emission and potentially in reception, the corresponding gains, and other aspects.

A set of emission delay time values, EDTn (n=1, 2, 3, . . . , N), of the focused and unfocused wavefront may be determined in different ways. One example is a three-step determination. Taking the example focused mode as depicted in FIG. 17, N is 7, the total number of firing elements 282 for the predetermined operational mode. First, determining the set of delays includes determining the distance 281 from the firing elements 282 to a virtual geometrical center of focusing point 296 at a certain time after each of the elements 282 are fired with delays. The furthest element 297 from the geometrical center 296 in this example is located at the lowest position 297 in FIG. 17. Next, the travel time corresponding to each firing element 282 to the focusing point 296 is determined by dividing each element distance 281 by wave propagation speed in well fluid. Then, the delay time of each firing element 282 is determined as the maximum wave propagation time at the furthest element 297 minus the propagation time for each element. The ultrasonic pulses excited at the elements 282 each excite a circular wave front 299, which collectively form a convex wave front (or iso-phase) 294 seen from the focusing point 296. Depending on numbers of environmental parameters, including wave propagation speed in well fluid, total number of firing elements 282, geometrical parameters of the tool 280 and the casing/borehole wall 284, a set of delay time values may be revised each measurement.

A set of reception delay time values, RDTn (n=1, 2, 3, . . . , N), for signal reception can be also applied. If enhanced signal reception from the transmission focusing point 296 in FIG. 17 is sought, signal reception delay time can be set for each element as the travel time from each element minus the minimum travel time for the firing elements 282.

For emission and reception, different amplitude or gain can be applied to each element 282. A set of emission gain values, EGNn (n=1, 2, 3, . . . , N), and reception gain values RGNn (n=1, 2, 3, . . . , N), can be set at an arbitrary value, including 0. In FIG. 17, seven elements (N=7) operation is illustrated as an example. If transmission is to use seven elements and reception is to use the central three elements, then EGNn=[1, 1, 1, 1, 1, 1, 1] and RGNn=[0, 0, 1, 1, 1, 0, 0]. Recording of data from reception gain 0 element may be omitted to minimize downhole memory usage. For transmission and reception minimizing side lobe excitation, it is also possible to apply arbitrary weighting to EGNn and RGNn utilizing, for example, a Gaussian window that has maximum value at the central element(s), such as RGNn= [0.044, 0.249, 0.707, 1.000, 0.707, 0.249, 0.044], among other examples.

When conducting an azimuthal imaging acoustic measurement, a measurement may comprise several transmissions and receptions of acoustic signals with different transmitter/receiver sets in order to repeat the transmission/reception operation at different azimuths. The sequence of the transmission/reception operations may also be part of the variable sets for a measurement. Generally, when a measurement comprises a plurality of transmission/reception operations, the phased array modules may be configured so that the operational mode and the number of transmitters/receivers associated to each transmission/reception operation is the same, and the delays and gains may be set so that the waveform generated by each transmission/reception operation has the same wavefront profile.

To conduct emission and reception of a seven elements operation with azimuthally different elements, an emission elements index EIDn (n=1, 2, 3, . . . , N) and a reception elements index RIDn (n=1, 2, 3, . . . , N) can be varied. The phased array elements have an element index k (k=1, 2, 3, . . . , K, where K is the total number of elements of the array), such that the enabled emission and reception elements can be selected using a set of indices. For example, a pulse-echo mode operation may use an example phased array as depicted in FIG. 6. The pulse-echo measurements may be performed using a total of seven elements, rotating the active elements in the azimuthal direction starting from the central element of index 1 by changing EIDn and RIDn 32 times, such as [30, 31, 32, 1, 2, 3, 4], [31, 32, 1, 2, 3, 4, 5], [32, 1, 2, 3, 4, 5, 6], . . . , [28, 29, 30, 31, 32, 1, 2], [29, 30, 31, 32, 1, 2, 3], where numbers in bold indicate the central element in each active group of elements.

If pitch-catch measurements are to be performed in the azimuthal direction, using two groups of elements in the example array depicted in FIG. 6, for example, the EIDn can be changed as described above in the pulse-echo example, and the RIDn may be changed 32 times, such as [30, 31, 32, 1, 2, 3, 4]+n1, [31, 32, 1, 2, 3, 4, 5]+n1, [32, 1, 2, 3, 4, 5, 6]+n1, . . . , [28, 29, 30, 31, 32, 1, 2]+n1, [29, 30, 31, 32, 1, 2, 3]+n1, where n1 is an integer that specifies azimuthal separation of the receiving group elements. For example, if n1=8, the azimuthal angular distance between the emission and reception groups will be 90 degrees. Assuming pitch-catch measurements use the example phased arrays depicted in FIG. 46, with one transmitter array 326 and four receiving arrays 328, and each phased array consists of identical 32-element phased array example discussed above, the n1 value can be set so as to select desired elements grouped in desired phased array. As an example, the elements can be indexed from 1 to 160, such as [1, 2, 3, . . . , 32] for the transmitter array 326 and [33, 34, 35, . . . , 64], [65, 66, 67, . . . , 96], [97, 98, 99, . . . , 128], and [129, 130, 131, . . . , 160] for the receiving arrays 328, from the bottom to top, having the first element at the identical azimuth angle. To perform pitch-catch measurements using, for example, emission from the transmitter array 326 and reception in the second receiver array 328 from the bottom, the EIDn may be [30, 31, 32, 1, 2, 3, 4] and the RIDn may be [30, 31, 32, 1, 2, 3, 4]+n1, where n1=64. However, these are merely examples to explain one of possible control methods and parameter values. Alternative methods are also within the scope of the present disclosure.

Figure 18:
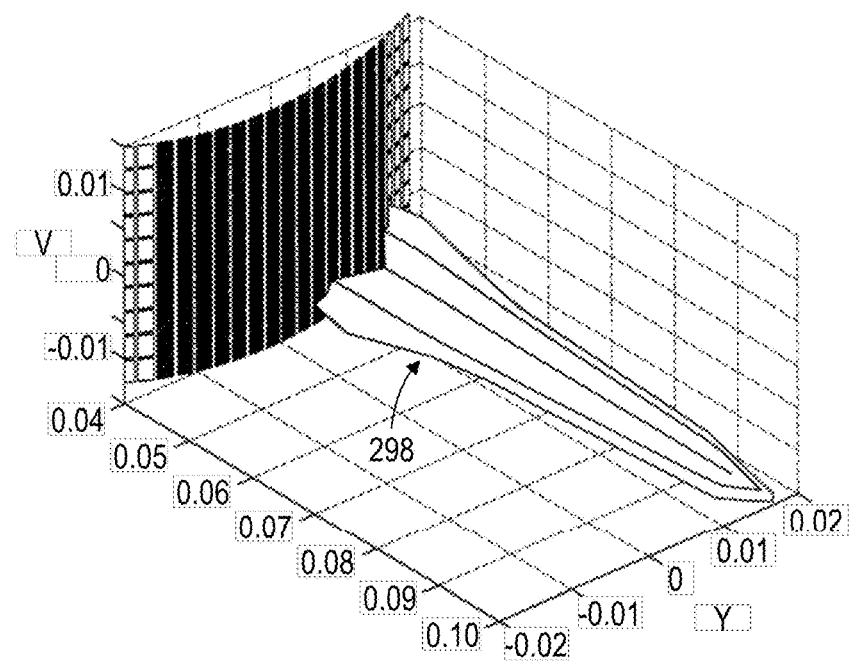
FIG. 18 is a perspective view of a phased array emitting an ultrasonic beam with azimuthal and axial focusing according to one or more aspects of the present disclosure.
Figure 19:
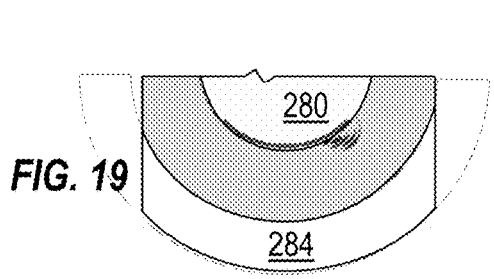
FIGS. 19-22 are axial views of a phased array measurement target and a phased array tool disposed in the target and emitting an azimuthally steered ultrasonic beam according to one or more aspects of the present disclosure.
Figure 20:
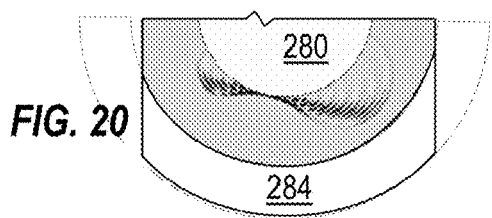
Figure 21:
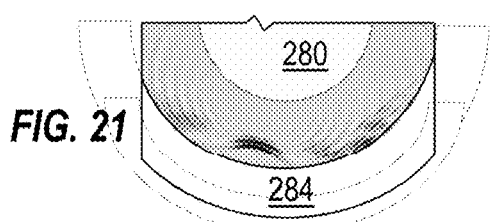
Figure 22:
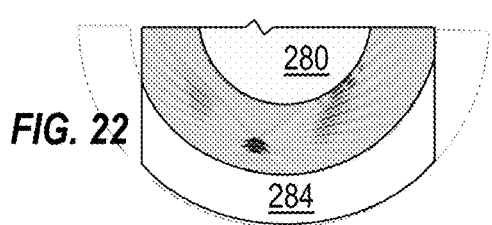

Such focusing may also be applied in the axial direction. For example, as depicted in FIG. 18, both azimuthal and axial focusing may be utilized to generate a focused beam 298.

Azimuthally and/or axially focused beams may also be steered azimuthally by applying the correct delays. FIGS. 19-22 successively depict an example steering of such a beam to the left (relative to the page) by applying non-symmetric temporal delays to the elements. In such operations, the emitting and receiving elements may be part of the same axially collocated phased array or axially offset and separated arrays. Such operations may also be combined with axially directed and undirected modes described below.

Figure 23:
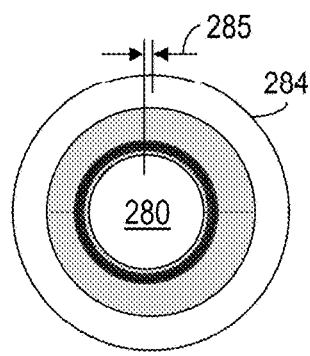
FIGS. 23-25 are axial views of a phased array measurement target and a phased array tool disposed in the target and emitting a flash mode ultrasonic beam according to one or more aspects of the present disclosure.
Figure 24:
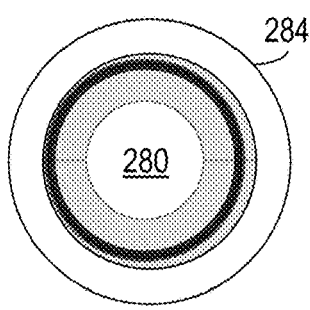
Figure 25:
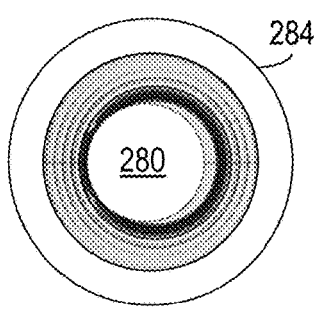

Phased arrays within the scope of the present disclosure may also be operated in flash mode, in which some or each of the elements distributed in the full circumference of the array are fired simultaneously to excite a circumferentially radiating wave, and the same or different set of elements distributed in the full circumferential receive the returning wave. An example is depicted in FIGS. 23-25, in which FIG. 23 depicts a signal just after emission from the phased array tool 280, FIG. 24 depicts the signal just before hitting the target 284, and FIG. 25 depicts the signal around the time of reception of the main specular echo at the phased array tool 280. In this example, the phased array tool 280 is slightly eccentered within the target 284, in that the center of the phased array tool 280 is offset in the −X direction from the center of the target 284 by a distance 285. A corresponding sinusoidal eccentering graph may be determined utilizing this flash mode, after which re-application of new delay laws may also be reinjected to the flash mode. In a particular implementation of the flash mode, the phased arrays are configured so that the wavefront profile contacts the borehole wall essentially at the same time all around the perimeter of the tool. However, other implementations are also within the scope of the present disclosure.

The flash mode can provide many types of measurements at a reduced azimuthal resolution. A possible advantage of the flash mode may be that logging could be very rapid because the full circumference is covered without electronic rotation of the beam. Operationally, this may be utilized to perform a quick first pass before deciding (automatically or with user interaction) where to re-log using measurements, such as to permit obtaining parameters of the wellbore or tool with higher resolution. Moreover, operational modes may be changed during logging (either automatically or by downlink) according to one or more aspects described below, such that the flash mode operation for eccentering correction (and/or other purposes) may be performed in the same logging pass as the high-resolution logging.

The emitting and receiving elements utilized during flash mode operations may be part of the same phased array or on axially separated arrays, such as when combined with an axial directed/undirected or focused mode. Where multiple phased arrays are utilized, the arrays may be separated by zero-distance, in which case they constitute one single larger array that combines the functionality of emission and reception.

Figure 26:
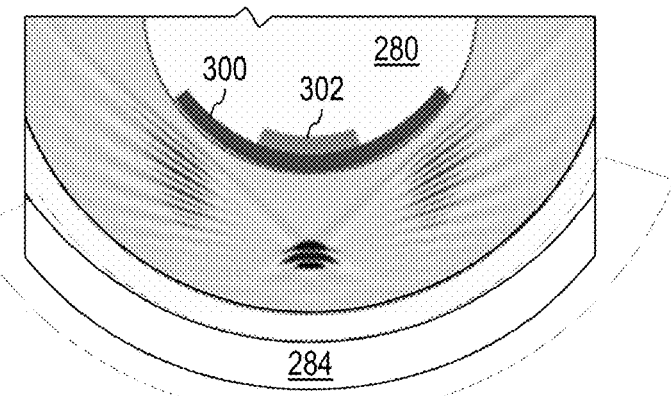
FIG. 26 is an axial view of a phased array measurement target and a phased array tool disposed in the target for pulse-echo operation utilizing more firing elements than receiving elements according to one or more aspects of the present disclosure.

Phased arrays within the scope of the present disclosure may also be utilized in separate firing reception modes, such as to optimize the conditioning of the waveform. For example, pulse-echo mode operation may be based on a set of receiving elements that is different from the set of transmitting elements. The firing elements 300 and receiving elements 302, which are illustrated as radially offset arrays in FIG. 26 for visualization purposes, are two different parts of azimuthal elements of the same phased array, 206 in FIGS. 2 and 262 in FIG. 6.

Figure 27:
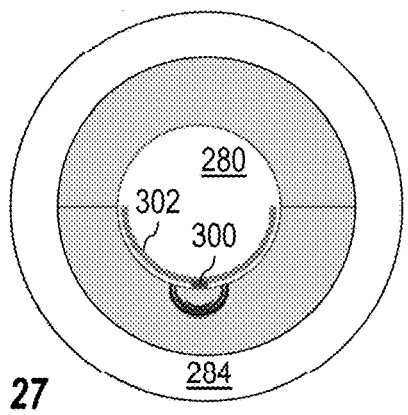
FIGS. 27-32 are axial views of a phased array measurement target and a phased array tool disposed in the target for pulse-echo operation utilizing more receiving elements than firing elements according to one or more aspects of the present disclosure.
Figure 30:
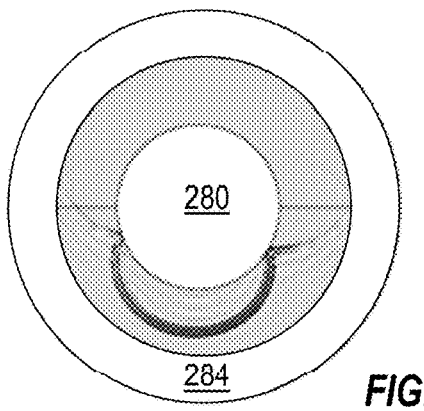
Figure 28:
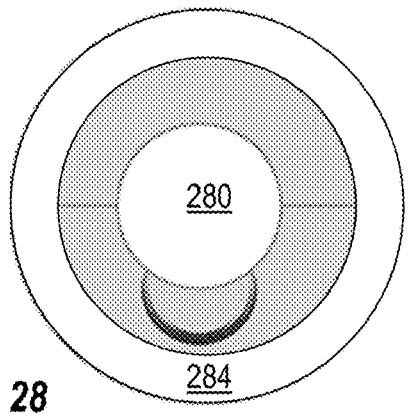
Figure 31:
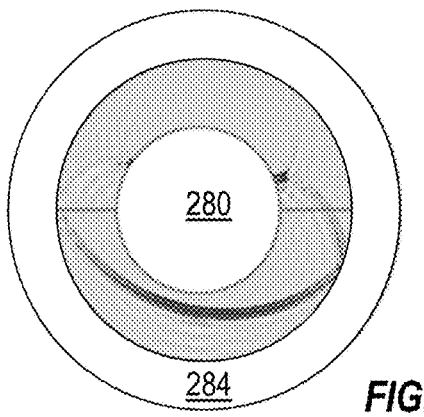
Figure 29:
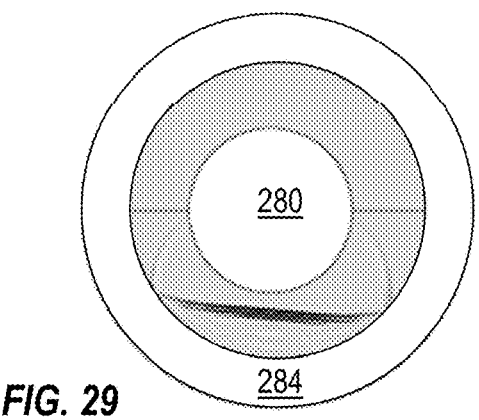
Figure 32:
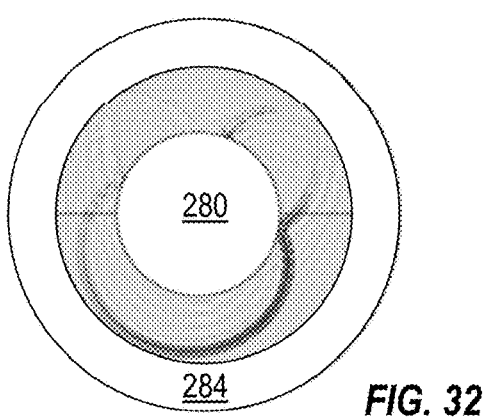

Alternatively, a scheme can also be used where one (or a few) element 300 is fired and multiple elements 302 are receivers, wherein the waveforms of each of the receiving elements 302 are sent/stored separately, as depicted in FIGS. 27-32. FIG. 27 depicts the signal just after firing a single element 300, FIG. 28 depicts the signal just before hitting the target 284 for the first time, and FIG. 29 depicts the signal just before coming back to the phased array tool 280. FIG. 30 depicts the signal enveloping the phased array tool 280 and hitting the target 284 for the second time, FIG. 31 depicts the signal further enveloping the phased array tool 280, and FIG. 32 depicts the signal fully enveloping the phased array tool 280, at which time all of the receiving elements 302 have registered the first target echo. In the example depicted in FIGS. 27-32, the number F of firing elements 300 equals one, but the firing element-section may also span two, three, four, or five firing elements 300, among other examples within the scope of the present disclosure.

In such operations, the emitting and receiving elements may be part of the same phased array or on axially separated arrays. Additionally, while such operations may utilize greater bandwidth and/or memory capacity relative to other operations, such operations may be advantageous in that, for example, the operations may be regenerated in post-processing utilizing linear combinations of the received waveforms.

Figure 33:
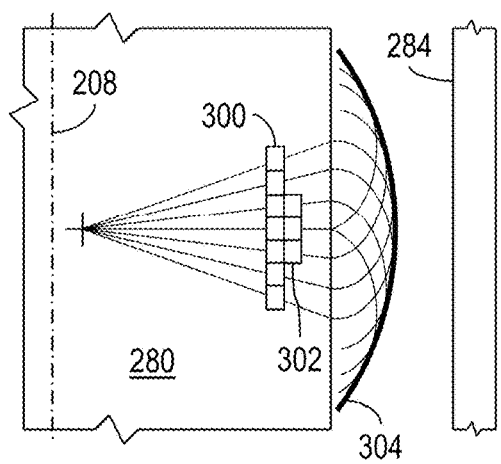
FIG. 33 is a side view of a phased array measurement target and a phased array tool disposed in the target and emitting an ultrasonic beam with a convex wavefront for pulse-echo mode operation utilizing more firing elements than receiving elements according to one or more aspects of the present disclosure.
Figure 34:
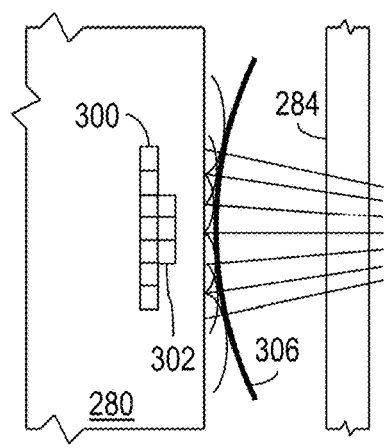
FIG. 34 is a side view of a phased array measurement target and a phased array tool disposed in the target and emitting an ultrasonic beam with a concave wavefront for pulse-echo mode operation utilizing more firing elements than receiving elements according to one or more aspects of the present disclosure.

The separation of firing elements 300 and receiving elements 302 may also be in the axial direction, such as in the examples depicted in FIGS. 33 and 34. A number F of firing elements are part of axial elements, such as elements 204 in FIG. 2. The firing elements 300 and a number R of receiving elements 302 are illustrated as radially offset arrays for visualization purpose, however, they are two different sets or parts of the same array. The number R is about a half of number F in FIGS. 33 and 34, although other ratios of R:F are also within the scope of the present disclosure, depending on measurements modes. FIG. 33 depicts a wavefront 304 that is convex relative to the central longitudinal axis 208 of the phased array tool 280, and FIG. 34 conversely depicts a concave wavefront 306. However, while FIGS. 33 and 34 depict convex and concave wavefront examples, separated emitting and receiving elements may also be utilized to generate linear and otherwise shaped wavefronts within the scope of the present disclosure. Additionally, while FIGS. 33 and 34 depict the number F of firing elements 300 being greater than the number R of receiving elements 302, other implementations within the scope of the present disclosure may include a number F of firing elements 300 that is less than the number R of receiving elements 302.

Figure 35:
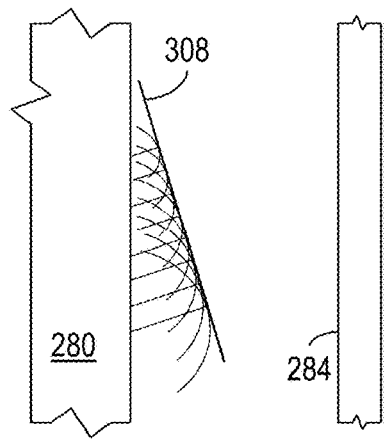
FIG. 35 is a side view of a phased array measurement target and a phased array tool disposed in the target and emitting an ultrasonic beam with a linear wavefront having a lower incident angle according to one or more aspects of the present disclosure.
Figure 36:
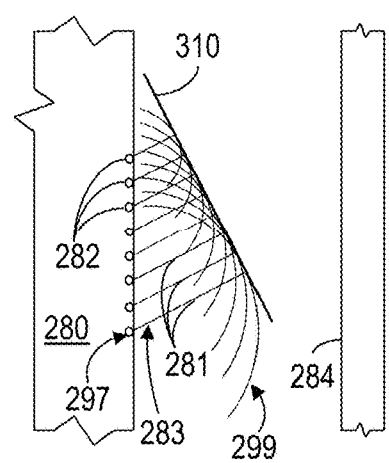
FIG. 36 is a side view of a phased array measurement target and a phased array tool disposed in the target and emitting an ultrasonic beam with a linear wavefront having a higher incident angle according to one or more aspects of the present disclosure.
Figure 37:
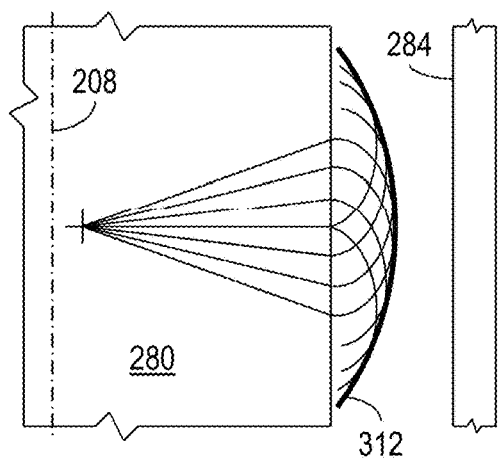
FIG. 37 is a side view of a phased array measurement target and a phased array tool disposed in the target and emitting an unfocused ultrasonic beam with a convex wavefront according to one or more aspects of the present disclosure.
Figure 38:
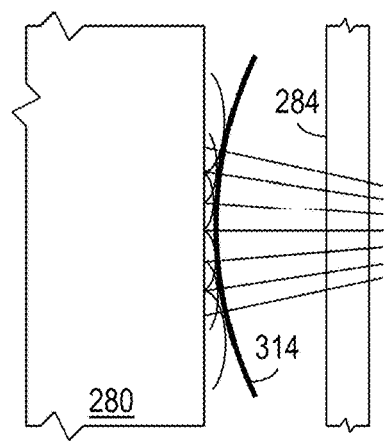
FIG. 38 is a side view of a phased array measurement target and a phased array tool disposed in the target and emitting a focused ultrasonic beam with a concave wavefront according to one or more aspects of the present disclosure.

FIGS. 35-38 pertain to longitudinally directed and undirected modes (transmission and reception) according to one or more aspects of the present disclosure. For example, FIGS. 35 and 36 depict example linear wavefronts 308 and 310 steered at two different angles relative to the wellbore radial axis (+X), corresponding to longitudinal steering mode. Low and high angle wavefronts may be utilized to selectively excite respectively fast and slow propagating acoustic waves, such as for extensional or flexural modes in the casing. FIGS. 37 and 38 depict example convex (312) and concave (314) wavefronts (respectively longitudinally unfocused and focused) that may be utilized to excite multiple casing modes at the same time.

For example, the convex wavefront 312 may be utilized to excite multiple casing modes at the same time, such as the extensional and flexural modes at the same time as a casing-thickness mode. Excited signals may be measured at a controlled axial distance, and the multi-modal signals may be processed by applying slowness extraction techniques, such as first motion detection (e.g., as described in U.S. Pat. No. 7,675,813, the entirety of which is hereby incorporated herein by reference), slowness-time coherence (e.g., as described in U.S. Pat. No. 4,594,691, the entirety of which is hereby incorporated herein by reference), and/or modified Prony's methods (e.g., as described in U.S. Pat. No. 6,614,716, the entirety of which is hereby incorporated herein by reference), among other examples. Concave wavefronts may be utilized to interrogate the casing or borehole surface at finer special resolution compared with line or convex wavefronts because, for example, a concave wavefront may be focused to some degree at the inner surface of the casing/borehole.

Similar to focused and unfocused modes, delay time values of the steered linear wave front 310 can be computed in different ways, and one example is three-step computation taking an example steering mode in FIG. 36. First, compute distance 281 from firing elements 282 to a steered linear wave front 310 at certain time after all elements being fired with delays. The largest distance 283 is at the furthest element 297 from the linear wave front 310 in this example locating at the lowest position 297 in FIG. 36. Secondly, travel time of each firing elements 282 to the linear wave front 310 is computed by dividing each element distance 281 by wave propagation speed in well fluid. Thirdly, delay time of each firing element 281 is computed as the maximum wave propagation time at the furthest element 297 minus propagation time of each element. An ultrasonic pulse, being excited at each element propagates as circular wave front 299, and then the pulses from all firing elements 282 eventually form linear wavefront (or iso-phase) 310.

Additionally, the axial or longitudinal modes described herein may be combined with the azimuthal steering and focusing modes according to aspects of the present disclosure. That is, even though wavefront profiles depicted in FIGS. 13-17 are in the azimuthal plane (normal to the tool axis), and wavefront profiles depicted in FIG. 35-38 are in the longitudinal plane (including the tool axis), the modes may generate 2D wavefront profiles in a longitudinal plane (as described below in conjunction with FIGS. 35-38) or, when both focusing are combined, for generating three-dimensional (3D) wavefront profiles. These and other combinations permit many different measurements, each being specific in terms of signal strength and conditioning, azimuthal resolution, and/or attainable logging speed, among other aspects.

The measurements described herein may be calibrated before the measurement job, during the job, or both. Such calibration may comprise element-by-element amplitude and/or sensitivity calibration. Denoising calibration may also or instead be utilized, such as via utilization of collar-section waveforms (e.g., as described in U.S. Pat. No. 10,114,138, the entirety of which is hereby incorporated by reference) and/or coherent noise-reduction techniques. Calibration may also be performed downhole, such as via pulse-echo transducer internal ringing baseline noise removal, among other examples. These and/or other calibration methods may be implemented in-situ and/or pre-calibration before the measurement job.

The following description pertains to the measurement capabilities that may be achieved via the stacking and on-the-fly programming of phased arrays according to one or more aspects of the present disclosure, including the different modes in which the phased arrays may be operated. The examples described below may be presented in the context of cased-hole measurements, but it should be understood that such examples are also applicable or readily adaptable to open-hole measurements, and vice versa.

Pulse-echo measurements utilizing phased arrays according to one or more aspects of the present disclosure may include surface echo/temporal thickness measurements, such as previously obtainable by Schlumberger's Ultrasonic Casing Imager tool (UCI), as well as thickness mode measurements, such as previously obtainable by Schlumberger's UltraSonic Imaging Tool (USIT). For example, using a single phased array, the focused and unfocused beams depicted in FIGS. 39-41 may provide measurements for corrosion and cement impedance.

FIG. 39 depicts a focused beam emitted by a predetermined number of elements 202 for higher azimuthal resolution, such as may be utilized for pulse-echo measurements. If applied with a high-frequency array, the radii and thickness measurements of the casing may be determined via temporal analysis of the waveform (e.g., first and second echo detection). Such focused beams may also be applied with a lower frequency, such as to account for attenuative borehole fluids ("muds"), although the precision of the thickness measurement may be compromised.

FIG. 40 depicts an unfocused beam emitted by a predetermined number of elements 202 with low oblique reflection, such as may be utilized for spectral analysis at lower frequencies. Such operation may provide very high precision thickness and cement impedance results.

FIG. 41 depicts an unfocused beam emitted by a predetermined number of elements 202 for resolution with normal incidence. Such modes are in between the focused and unfocused variants described above, such as for a Focus 2L mode where L is the distance between the casing internal diameter and the outer surface of the phased array tool 280. These "in-between" modes may be utilized to obtain a compromise between precision of the thickness/cement measurement and the azimuthal resolution of the radius measurement.

The above-described F-R modes (whether F<R or F>R) may be utilized in combination with the focused or unfocused beams depicted in FIGS. 39-41. For example, the F-R modes may be combined with focused and/or unfocused beams to improve the received signal and/or for full post-processing capabilities.

The focused and unfocused beams depicted in FIGS. 39-41, including in combination with the F-R modes, may utilize firing elements axially offset from receiving elements in a single phased array, or the firing elements may be in a first phased array while the receiving elements may be in one or more second phased arrays.

The operational modes above have been indicated as appropriate for obtaining measurement of certain properties of the wellbore. However, other operational modes may be used to obtain the same properties or other properties.

The above-described flash mode may also be utilized with the pulse-echo measurements to, for example, provide corrosion and cement measurements. In such implementations, the azimuthal resolution may be reduced, but the measurements may be made at higher logging speeds because the beam isn't rotated to obtain full azimuthal coverage.

One or more of the pulse-echo measurements describe hereinabove may be utilized in open-hole implementations to, for example, provide surface-reflectivity for imaging borehole features and textures, acoustic impedance measurements, and caliper measurements at high-resolutions. However, other open-hole implementations are also within the scope of the present disclosure.

Pitch-catch measurements utilizing phased arrays according to one or more aspects of the present disclosure, whether with or without axial steering, may include flexural mode measurements, such as previously obtainable by Schlumberger's Isolation Scanner tool, as well as extensional mode measurements, such as described in U.S. Pat. No. 10,364,664, the entirety of which is hereby incorporated herein by reference. For example, flexural and extensional mode measurements may be performed as depicted in the example implementations shown in FIGS. 42 and 43. In FIG. 42, a lower-angle steering is utilized for strong excitation of extensional mode being refracted at the critical angle (or π/2 radian) in a casing (indicated in FIG. 42 by reference number 316 in contrast to weak flexural mode 318) via faster mode/wave excitation, perhaps utilizing Equation (7) set forth below.

$$\frac{\sin(\theta)}{V_f} = \frac{\sin(\pi/2)}{V_{fast}} \quad (7)$$

where θ is the steering angle illustrated in FIG. 42, $V_f$ is the speed of sound in the borehole fluid occupying the annulus defined between the phased array tool 280 and the casing 120, and $V_{fast}$ is the speed of fast waves that may be propagating in the borehole, such as P-waves or compressional waves of the formation or casing extensional mode in the casing. In FIG. 43, a higher-angle steering is utilized for strong flexural mode measurements (indicated in FIG. 43 by reference number 320 in contrast to weak extensional mode 322) via slower mode/wave excitation, perhaps utilizing Equation (8) set forth below.

$$\frac{\sin(\theta)}{V_f} = \frac{\sin(\pi/2)}{V_{slow}} \quad (8)$$

where θ is the steering angle illustrated in FIG. 43 and $V_{slow}$ is the speed of slow waves that may be propagating in the borehole, such as shear waves or their associated modes of the formation, or flexural waves in the casing.

The flexural and extensional-wave measurements may be performed with multiple phased arrays stacked axially within a phased array tool. For example, the phased array tool 280 may comprise a single transmitter for a non-compensated implementation, in which at least three phased arrays are stacked to obtain a TX-RX-RX (-RX-RX, etc.) configuration, wherein the at least two receivers are utilized to provide attenuation measurements. However, the phased array tool 280 may comprise a dual transmitter for a compensated implementation, in which at least four phased arrays are stacked to obtain a TX-RX-RX (-RX-RX, etc.)-TX configuration. In such dual transmitter implementations, known as "borehole-compensation" (such as described in U.S. Pat. No. 3,524,162 or 10,364,664, the entire disclosures of which are hereby incorporated herein by reference), the same measurements are made separately with two transmitters so as to decrease or eliminate the impacts of transmitter outputs and receiver sensitivities and/or geometrical tilt of the phased array relative to the borehole wall on the measurements.

Both flexural and extensional wave measurements may also have the potential to provide third interface echo (TIE) information from the ultrasonic penetration of a first casing and reflection of a second casing or formation. The TIE processing may be utilized for two casings and/or formation-behind-casing implementations. These axial pitch-catch measurements may be obtained with or without azimuthal focusing, potentially combined with few-to-many (F<R) or many-to-few (F>R) modes. Such axial pitch-catch measurements may also be utilized with a flash mode to obtain quick low-resolution logs.

For open-hole implementations, P- and S-waves (or associated modes) may also provide information on the formation slowness characteristics and may be utilized for imaging applications. The same phased-array stack may be utilized, in which the angular steering is adapted to be optimized for the S- and P-wave speeds of the formation.

Pitch-catch measurements utilizing may also be utilized for multi-modal velocity dispersion and attenuation analysis (e.g., as described in U.S. Pat. No. 9,534,487, the entirety of which is hereby incorporated herein by reference), as depicted in the example implementation shown in FIG. 44. For example, for the flexural and extensional-wave measurements, the same single-transmitter non-compensated and dual-transmitter compensated configurations may be utilized. The measurements may also provide TIE information on a second casing or formation. Such axial pitch-catch measurements may be obtained with or without azimuthal focusing, potentially combined with few-to-many or many-to-few modes. The measurements may also be utilized wih a flash mode to obtain quick low-resolution logs.

For open-hole implementations, the multi-modal pitch-catch measurements may also provide information on the formation slowness characteristics and may be used for imaging applications. The same phased-array stack may be utilized with and without the second transmitter to compensate borehole wall geometrical tilt relative to the receiving phased array axis.

Figure 45:
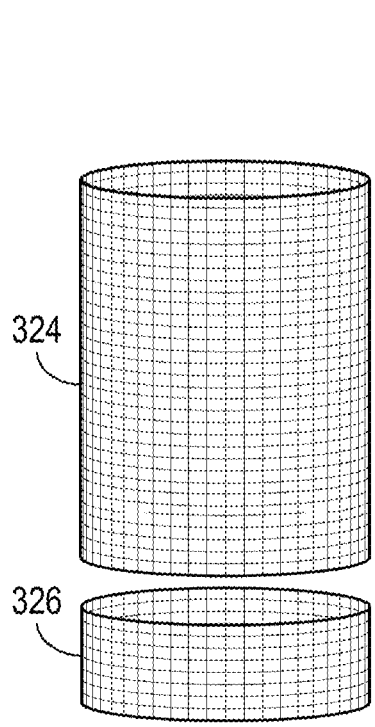
FIG. 45 is a perspective view of at least a portion of an example implementation of an arrangement of phased arrays according to one or more aspects of the present disclosure.
Figure 46:
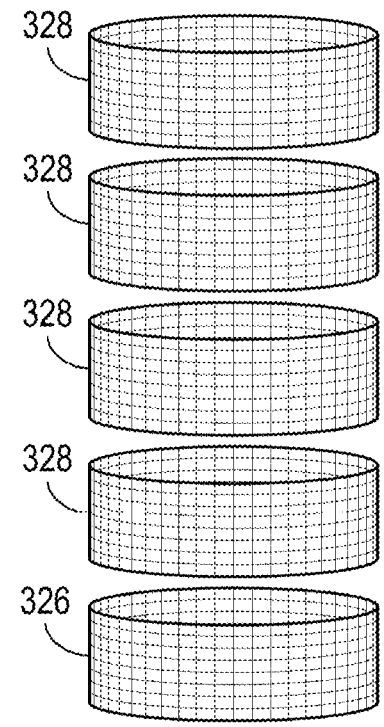
FIG. 46 is a perspective view of at least a portion of another example implementation of an arrangement of phased arrays according to one or more aspects of the present disclosure.
Figure 47:
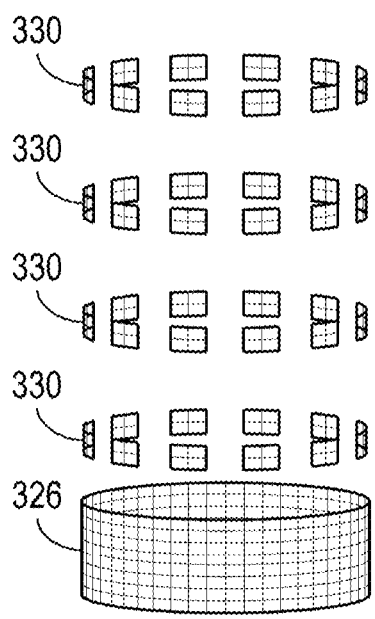
FIG. 47 is a perspective view of at least a portion of another example implementation of an arrangement of phased arrays according to one or more aspects of the present disclosure.
Figure 48:
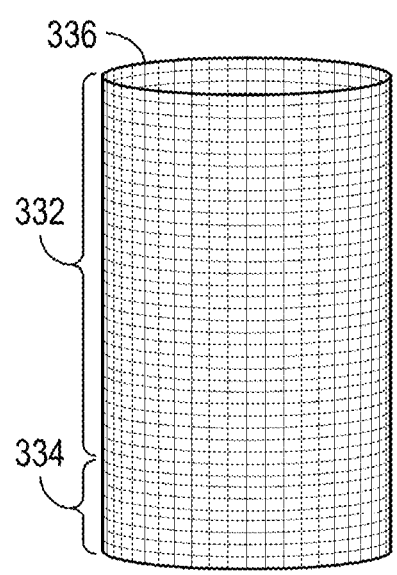
FIG. 48 is a perspective view of at least a portion of another example implementation of an arrangement of phased arrays according to one or more aspects of the present disclosure.

The modes, operations, and measurements described above may utilize a receiving section that can take many forms, such as the examples depicted in FIGS. 45-48. FIG. 45 depicts an example receiving section formed by a single larger multi-element phased array 324 axially separated from a transmitting array 326. FIG. 46 depicts an example receiving section formed by a plurality of stacked phased array 328. FIG. 47 depicts an example receiving section formed by a plurality of point-wise arrays 330 in which each receiver arrays 330 has very few elements (or perhaps just one element). FIG. 48 depicts an example receiving section 332 and transmitting section 334 formed by a single phased array 336. The example receiving sections 324, 328, 330, 332 depicted in FIGS. 45-48 may be connected to acquisition electronics 210 (as described above), whether with or without transmitter components 216 and TX/RX switches 220. Acquisition electronics 210 may apply reception delay (perhaps including 0 delay) for signal reception, in the similar way as transmission beam steering, either during hardware signal acquisition by acquisition electronics 210 or during digital signal processing of memory data at the surface.

Aspects of the present disclosure also pertain to combination pitch-catch and pulse-echo measurements with azimuthal steering utilizing a single array. Such measurements may be utilized for vertical casing fracture/break detection, such as described in U.S. Pat. No. 10,126,454, the entire disclosure of which is hereby incorporated by reference. By applying beam steering to a focused firing, different elastic propagation modes may be induced in an azimuthal sense. Such measurements may be utilized to detect vertical (axial) features. When performed with a single phased array, the same elements that fire may be used to receive, or different elements may be utilized for receiving.

Figure 49:
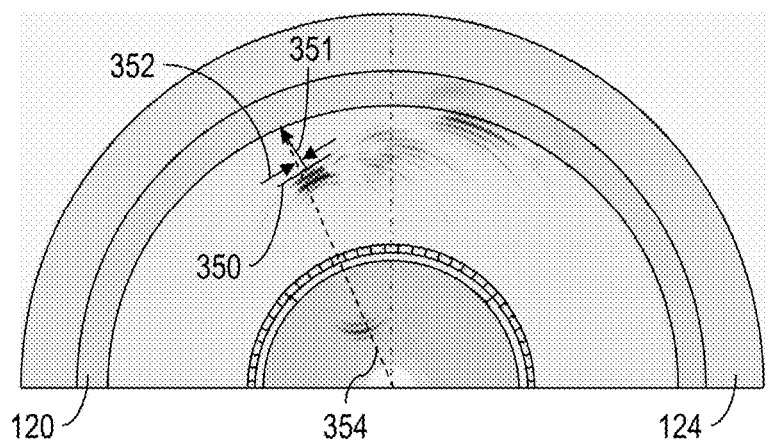
FIGS. 49 and 50 are axial views of a phased array measurement target and a phased array tool disposed in the target for combination pitch-catch/pulse echo operation with lower-angle steering at different times according to one or more aspects of the present disclosure.
Figure 50:
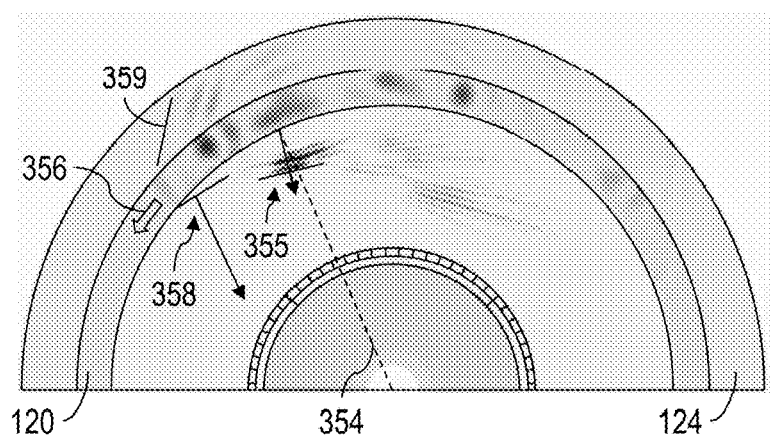

An example excitation of azimuthally propagating fast mode in a cemented casing 120 is depicted in FIG. 49, utilizing a wavefront 350 at a low steering angle ($\theta$) 352 at time $T_o$. The steering angle 352 is depicted as the angle between a radial axis 354 and a propagation vector 351 normal to the wavefront 350, wherein the radial axis 354 and the propagation vector 351 intersect at the inner surface of the casing 120. FIG. 50 represents the same example at time $T_o+t$, including the primary specular reflection 355, an azimuthally propagating extensional wave 356 excited by the initial emission (350), an azimuthally propagating fast casing mode 356 radiating or refracting energy 358 in fluid inside the casing 120, and an azimuthally propagating wave 356 radiating or refracting energy 359 in the cement 124 outside the casing 120.

Figure 51:
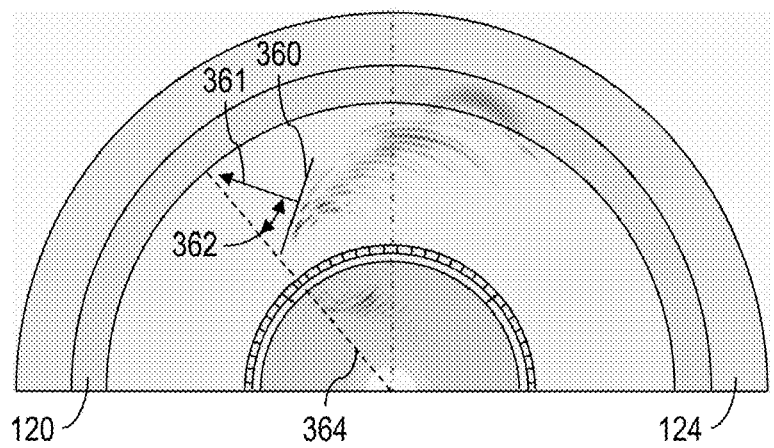
FIGS. 51 and 52 are axial views of a phased array measurement target and a phased array tool disposed in the target for combination pitch-catch/pulse echo operation with higher-angle steering at different times according to one or more aspects of the present disclosure.
Figure 52:
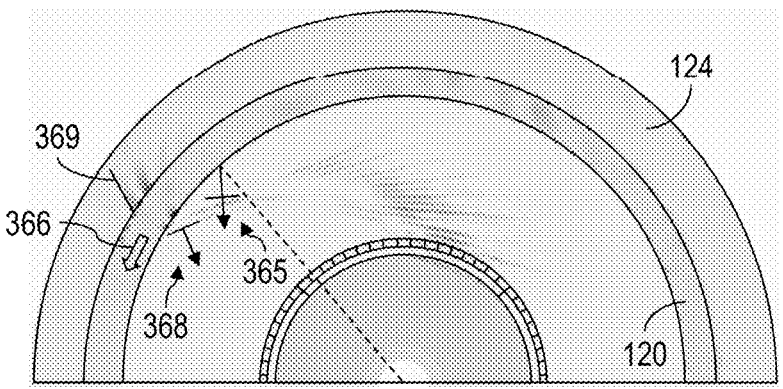

An example excitation of azimuthally propagating slow mode in the cemented casing 120 is depicted in FIG. 51, utilizing a wavefront 360 at a high steering angle ($\theta$) 362 at time $T_o$. The steering angle 362 is depicted as the angle between a radial axis 364 and a propagation vector 361 normal to the wavefront 360, wherein the radial axis 364 and the propagation vector 361 intersect at the inner surface of the casing 120. FIG. 52 represents the same example at time $T_o+t$, including the primary reflection 365, an azimuthally propagating extensional wave 366 excited by the initial emission 360, an azimuthally propagating slow mode 366 radiating or refracting energy 368 in fluid inside the casing 120, and the azimuthally propagating casing mode 366 radiating or refracting energy 369 in the cement 124 outside the casing 120.

FIGS. 49-52 demonstrate that the energy of propagating modes, which changes as a function of changes of acoustic properties of material (cement 124) or its defects (not illustrated but can be replaced by fluid or gas) outside the casing 120, or/and defects in the casing 120 (e.g., corrosion and fractures), can be measured utilizing refracted waves (e.g., 358, 368). Such measurements may be utilized for cement and casing corrosion evaluation in similar way as they were applied to the axially propagating casing extensional modes that have been used for cement bond logging (CBL) and casing flexural mode measurements. For openhole implementations, this mode may be utilized for detecting vertical fractures or other vertical formation events, whether they are drilling induced or of natural origin, and/or P- and S-waves (or associated modes) speed measurements.

Aspects of the present disclosure also pertain to pitch-catch combinations of azimuthal and axial modes. For example, spiral modes may be generated by transmitting axially and azimuthally steered beams. The principles of such measurements are the same as described above, except that the receiving array is axially spaced from the emitting array, and the beam is steered axially and azimuthally.

By combining phased array sections as described above, aspects of the present disclosure provide the potential to combine the measurement modes and operational modes described above utilizing a single toolstring. The following description provides different example measurement types linked to the different example operational modes.

Figure 53:
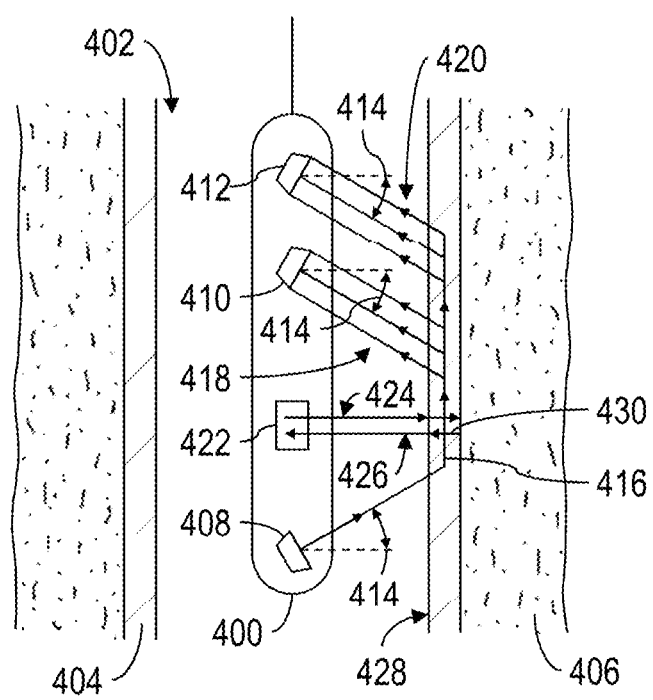
FIG. 53 is a side view of a conventional downhole tool.

FIG. 53 illustrates one example of a conventional tool 400 for cement evaluation in a borehole 402 in which a casing 404 is secured by cement 406, where such evaluation may be via the measurements and evaluation methods disclosed in U.S. Pat. No. 7,149,146, the entirety of which is hereby incorporated by reference. The conventional tool 400 is equipped with one set of pitch-catch sensors that consists of a transmitter 408 and two receivers 410, 412, of which orientation angles $\theta$ are set at angle 414 to maximize flexural mode excitation 416 in the casing 404 through well fluid (not shown) and to maximize refracted flexural waves 418, 420 to the respective receivers 410, 412 at the same angle 414, and one pulse-echo sensor 422 that is oriented toward the casing 404 at a normal incident angle. While the flexural mode propagates 416 in the casing 404 at the distance identical to the spacing of the receivers 410, 412, the refracted flexural signal amplitude reduces. An attenuation rate of the signal can be determined as $ATT_f$ from the two measured amplitudes at the receivers 410, 412 and the known receiver spacing at a controlled distance. The flexural attenuation rate $ATT_f$ varies as a function F(Zf, Zc), where Zf and Zc are acoustic impedance of the well fluid and the cement 406 that are to be inverted as the final output of the measurements. The pulse-echo sensor 422 emits ultrasonic pulse 424 and receives echo 426 including the echo from the first casing-fluid interface 428, followed by casing ringing 430 or casing thickness mode. The casing ringing 430 signal is attenuated at the attenuation rate a as another function G(Zf, Zc) that has different sensitivity to the impedance Zf and Zc. One example inversion method is to use linear model relations that are represented as $ATT_f = k1*(Zf+Zc)$ and $\alpha = k2*Zf + k3*Zc$, where k1, k2, and k3 are proportionality factors that provide a unique solution, as detailed in U.S. Pat. No. 7,149,146. Bold letters above indicate unknown wellbore parameters to be inverted. Unique Zf and Zc can be obtained from the above formula, providing measured attenuation rates of $ATT_f$ and $\alpha$. The material state behind the casing 404, such as gas, fluid, or solid (i.e., cement), can be estimated by the acoustic impedance of Zc and/or one or more of the attenuation rates of $ATT_f$ and $\alpha$. Good cementing quality is ensured when expected acoustic impedance of solid (cement) is obtained at full casing azimuth at a predetermined depth interval. Remedial cementing and risks of zonal isolation of hydrocarbon (e.g., gas and oil) can be indicated when continuous fluid and gas presence is identified in a relatively large area.

Figure 54:
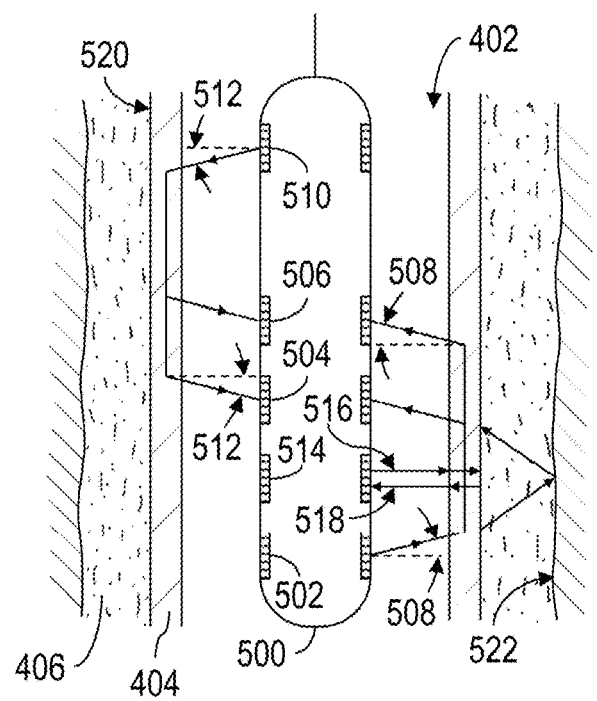
FIG. 54 is a schematic side view of at least a portion of an example implementation of apparatus according to one or more aspects of the present disclosure.
Figure 55:
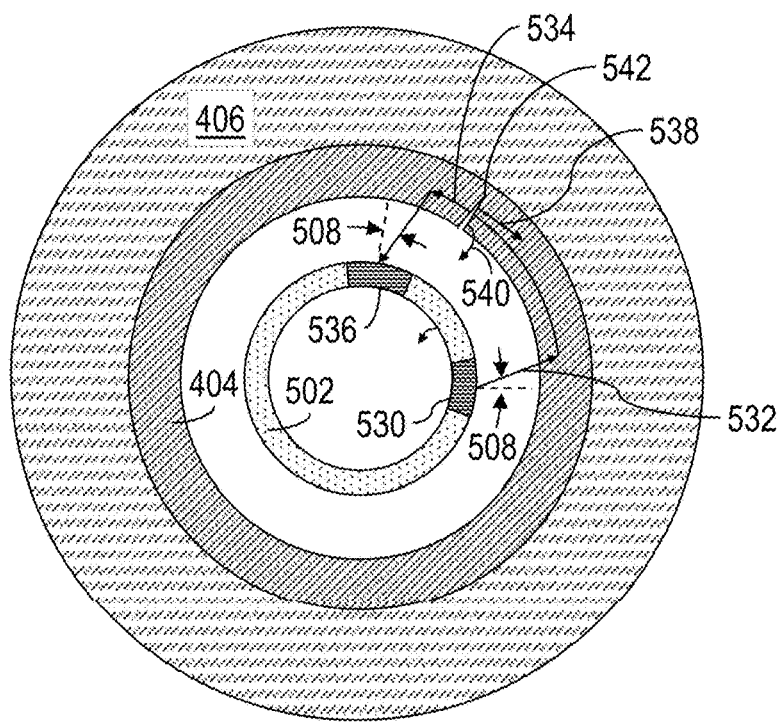
FIG. 55 is a schematic sectional view of the apparatus shown in FIG. 54.

FIGS. 54 and 55 illustrate an example configuration of a tool 500 comprising phased array sensors, as introduced in the present disclosure, to provide three types of measurements simultaneously. A first pitch-catch sensor consists of one transmitter array 502 and two receiver arrays 504, 506 to provide a first type of measurement, such as casing flexural mode. Transmission and reception are conducted at angle $\theta_f$ (designated in FIG. 54 by reference number 508) using delay values assessed to emit and receive a linear steered wave front. In a slim tubing or casing, the phased arrays permit efficient excitation of flexural mode at the angle $\theta_f$ that varies as a function of compressional wave propagation speed in well fluid (not shown) and flexural wave propagation speed in the casing 404 at operational ultrasonic frequency.

A second pitch-catch sensor consists of another transmitter array 510 and the two receiver arrays 504, 506 to provide a second type of measurement, such as casing extensional mode. Transmission and reception are conducted angle $\theta_e$ (designated in FIG. 54 by reference number 512) using delay values to emit and receive a linear steered wave front. Measurements can be conducted using two groups of transmission and receiving elements of the transmitter array 510 and receiver arrays 504, 506 that are 180 degrees apart in azimuth to minimize interference of up-going and down-going waves.

A third array 514 provides pulse-echo measurements via emitted pulses 516 and corresponding echoes 518. The third array 514 can be operated in two different operational modes. A first operational mode may interrogate the internal surface of the casing 404 using a focused wavefront for imaging the casing surface using the first casing echo, such as at a spatial resolution of about 2.5 millimeter (mm) beam diameter at 2.0 megahertz (MHz). A second operational mode may interrogate cement bonding at the casing-cement interface 520 using a unfocused, for instance cylindrical or linear, wavefront having peak energy (in term of frequency) near the casing resonance frequency, such as 480 kilohertz (kHz) at a casing thickness of about 6.4 mm. In other words, the frequency bandwidth of the wavefront in the second operational mode includes the casing resonance frequency. In the first operational mode, the arrival time of the reflected wavefront on the internal surface of the casing 404 (casing interface echo) used to derive the image of the casing. In the second operational mode the resonant tail of the wavefront reflected from the cement-casing interface (cement-casing interface echo) is analyzed via well-known techniques in order to derive information on casing thickness and cement bonding; The two different types of pulse-echo measurements may be for, respectively, (1) pit-and-hole evaluation (first operational mode) and (2) cement bonding and casing thickness evaluation applications, as a part of well integrity evaluation purposes (second operational mode). The conventional pulse-echo measurements using one transducer made of monolithic piezoelectric element cannot be operated in two different modes of focused and unfocused without replacing the transducer.

The second pitch-catch measurement provides casing extensional mode attenuation $ATT_e$ that varies as a function $E(Zf, Zc)$, which has relatively high sensitivity to cement acoustic impedance and cement bonding state. One possible inversion method (among other examples also within the scope of the present disclosure) is to use a linear relation, such as $ATT_e = k4*Zc$. The casing extensional mode is highly sensitive to cement bonding state, as well as miniscule gaps, often collectively referred to as microannulus, generally having thicknesses from tens to hundreds of microns and often introduced by hydraulic pressure changes in the well. The casing extensional mode attenuation rate can be highly reduced by microannulus. Microannulus can cause false alerts of low cementing quality. However, the miniscule gaps may be highly conductive to hydrocarbon in gas phase and may cause problems if the gaps are continuously present in large casing surface area. For ternary measurements of casing flexural, extensional, and thickness modes, respective inversion models can be modified, such as $ATT_f = k1*(Zf+Zc)$, $ATT_e = k4*Zc$, and $\alpha = k2*Zf + k3*Zc$ (among other examples also within the scope of the present disclosure). The linear coefficients k3 and k4 in bold letters may become variables of inversion. After inverting k3 and k4, the cement acoustic impedance, cement bonding state (such as perfect bond, microannulus state (gas- or fluid-filled), and its potential thickness) can be evaluated from k3 and k4 that will provide more precise cementing quality assessment including its bonding state. Acoustic reflection from the cement-formation boundary 522 can be also evaluated to indicate cement-formation bonding and casing eccentering in an open hole wellbore or in an outer casing (where multiple concentric casings exist).

FIG. 55 is schematic sectional view of the example tool 500 depicted in FIG. 54 depicting a concept of azimuthal measurement, in this example a flexural wave measurement, according to one or more aspects of the present disclosure. A first group 530 of elements in the phased array 502 excites a steered wavefront (not shown) toward the casing 404 at the direction 532 at incident angle $\theta_f$ (508) relative to the radial direction of the casing 404. The resulting flexural mode 534 propagates circumferentially within the casing 404 and is refracted to a second group 536 of receiving elements in the phased array 502 at the same angle $\theta_f$ (508). The amplitude of the flexural mode 534 may be deduced in a manner similar to as described above but at different sensitivity from axially propagating mode. The azimuthal flexural mode may be reflected 538 in the casing 404 and/or refracted 540 into well fluid when the casing 404 has defects, such as a vertical fracture 542 or defective cement,—such as channels (not shown) are present in the cement 406. Measurements of the azimuthally propagating wave attenuation $ATT_{af}$ provide one or more dimensions of cased hole well integrity assessment, such as via an inversion model function $H(Zf,Zc)$.

However, azimuthally propagating casing flexural mode is merely one example that may be achieved via operation of the tool 500 depicted in FIGS. 54 and 55, among other modes, operations, and tools within the scope of the present disclosure. The scope of the present disclosure is not limited to the examples described above with respect to FIGS. 54 and 55, and also includes other circumferentially propagating borehole wave measurements in a cemented casing or in an open hole. Additional examples within the scope of the present disclosure may be utilized as alternatives and/or adaptions of examples described in U.S. Pat. Nos. 9,625,599 and 10,126,454, the entire disclosures of which are hereby incorporated herein by reference.

Measurement interleaving may also be applied to implementations within the scope of the present disclosure, such that other measurement modules may be interleaved within the separate phased array modules. For example, a single toolstring may comprise more than one phased array tool, as described above, as well as other logging tools that provide measurements of different physics, such as electric, thermal, electromagnetic, pressure, fluid flow, nuclear, and/or other logging tools. These additional logging tools may be interleaved between the different phased array tools, such as in a modular manner.

Figure 56:
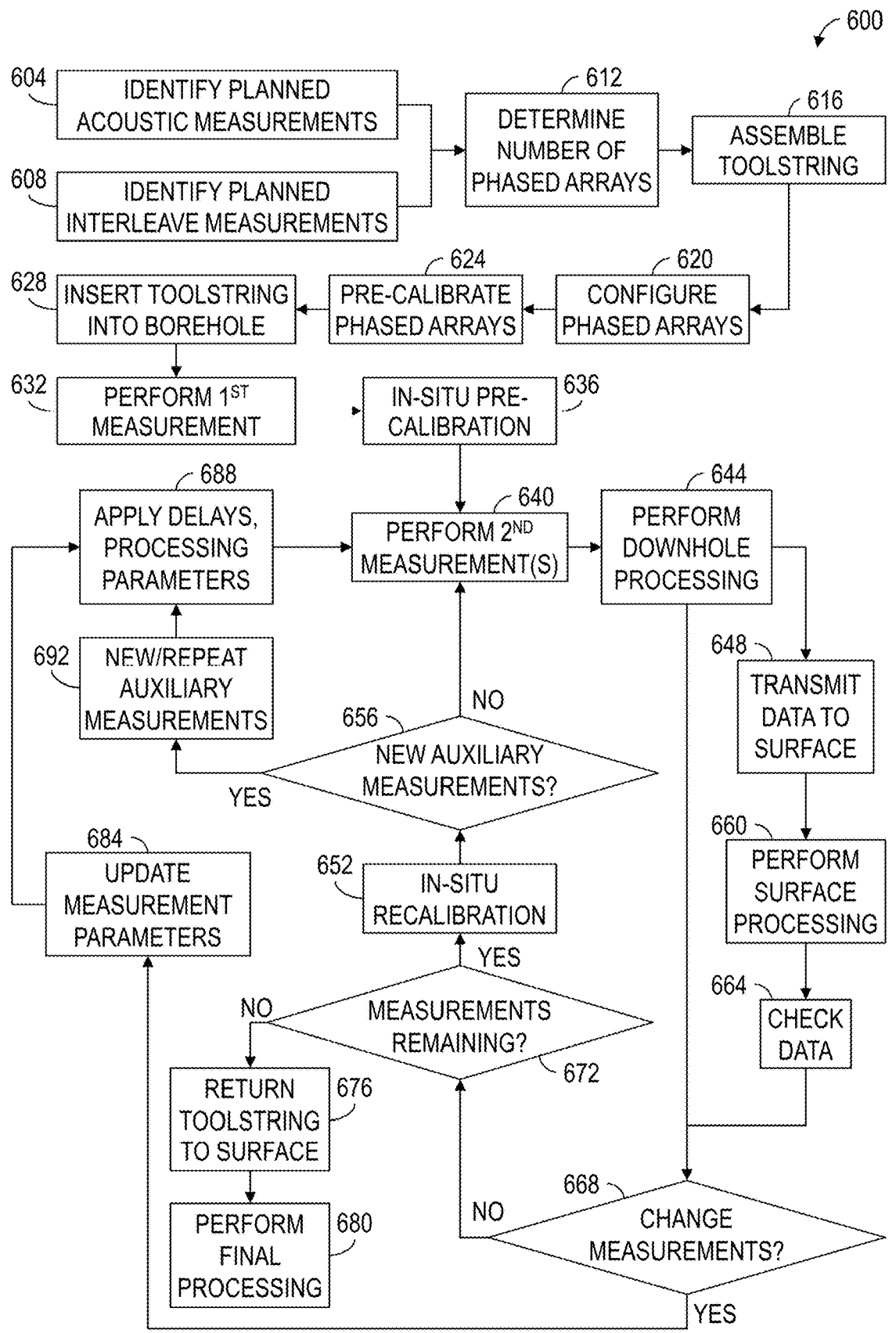
FIG. 56 is a flow-chart diagram of at least a portion of an example implementation of a method according to one or more aspects of the present disclosure.

FIG. 56 is a flow-chart diagram of at least a portion of an example implementation of a method 600 according to one or more aspects of the present disclosure. Other implementations of the method 600 also within the scope of the present disclosure, however, may not include each aspect described below, and may also include aspects other than as described below.

The method 600 comprises identifying 604 planned acoustic measurements to be performed with a number of phased arrays of a toolstring. The method 600 may also comprise identifying 608 planned interleave measurements. The planned acoustic measurements comprise a combination of the acoustic measurements described above. Each acoustic measurement comprises one or more transmission/reception in a predefined operational mode. A transmission/reception is defined by the number and relative positions of one or more transmitter arrays, the number and relative positions of one or more receiver arrays, their respective firing and receiving modes, and their associated variable sets. Each associated variable set includes at least a number of elements and their positions (or indices), pulse shape representing frequency for transmission, relative time delay, and gain or amplitude control of each element. The number and positions (or indices) of elements, delay, and/or gain may include 0 (or none), are to be set respectively for transmission and reception, for a phased array operation, disabling/enabling transmission and/or reception mode, focusing, and/or steering control, etc. The identification 604 of the planned acoustic measurements (and perhaps the identification 608 of the planned interleave measurements) may utilize a predetermined measurement plan.

As a first example (hereafter "Example A"), the identified 604 planned acoustic measurements may include (1) a first measurement comprising compensated, flexural measurement using an axially high-angle incident waveform, and (2) a second measurement comprising a pulse-echo measurement made at a first frequency and first axial position, and (3) a third measurement comprising a pulse-echo measurement made at a second frequency and second axial position. The different measurements may be obtained during a single, uphole trip of the toolstring within the borehole. In a variant, such measurements may be obtained during a downhole trip. As a second example (hereafter "Example B"), the identified 604 planned acoustic measurements may include a quick-log, non-compensated, extensional measurement using flash mode operation during a first uphole trip of the toolstring along a predetermined portion of the borehole. As explained below, the initial measurement plan may be refined to be followed by a second uphole trip of the toolstring, along at least a fraction of the predetermined borehole portion, for high-resolution, pulse-echo imaging of a section of the predetermined borehole portion that was identified during the first trip. The uphole trips are merely an example and can be replaced by downhole trip in arbitrary manner for the measurements.

The method 600 also comprises determining 612 a number of phased arrays to include in the toolstring that is sufficient to obtain each of the identified 604 acoustic measurements without removing the toolstring from the borehole. The determined 612 number may be the minimum number of phased arrays that can be utilized to obtain the identified 604 acoustic measurements. However, the determined 612 number may instead be the maximum number of phased arrays to be utilized to obtain the identified 604 acoustic measurements.

For example, with regard to the Example A, the determined 612 minimum number may be four phased arrays operated in a TX-RX-RX-TX arrangement (in which the uppermost and lowermost phased arrays are each operated as a TX and two phased arrays disposed between the TX arrays are each operated as an RX) for the flexural measurement, and two of the four phased arrays are operated for the pulse-echo measurements when those two phased arrays are not being operated to obtain the flexural measurement. Continuing with Example A, the determined 612 maximum number may be 2+N phased arrays (where N is an integer not less than 2) operated in a TX-N(RX)-TX arrangement (e.g., TX-RX-RX-RX-RX-TX if N=4) for the flexural measurement, and two additional phased arrays not utilized to obtain the flexural measurement are operated for the pulse-echo measurements. With regard to Example B, the determined 612 number may be three phased arrays operated in a TX-RX-RX arrangement for the extensional measurement while the toolstring is moved uphole in a first trip through a predetermined portion of the borehole, and one of the phased arrays is operated for the pulse-echo-measurement while the toolstring is moved uphole in a second trip through at least a fraction of the predetermined portion of the borehole. The toolstring may also comprise just one phased array module, such as when just a pulse-echo measurement is to be performed.

The method 600 also comprises assembling 616 the toolstring with the determined 612 number of phased arrays. The assembled 616 phased arrays may then be configured 620 according to the identified 604 acoustic measurements. For example, configuring 620 the assembled 616 phased arrays may comprise connecting the assembled 616 phased arrays to a processing system operable to execute operating software that contains a measurement plan describing the identified 604 acoustic measurements (and perhaps also describing the identified 608 interleave measurements). The measurement plan may have been utilized for the planned measurement identification 604, 608. Configuring 620 the assembled 616 phased arrays may then comprise commencing operation of the processing system, whereby the operating software communicates the measurement plan to the assembled 616 phased arrays and selects corresponding modes in which firmware and acquisition electronics associated with the assembled 616 phased arrays are to function to obtain the identified 604 acoustic measurements, as well as relative timing of the identified 604 acoustic measurements. For example, each of the assembled 616 phased arrays may comprise or otherwise be associated with a corresponding programmable circuit including an FPGA as described above, and configuring 620 the assembled 616 phased arrays may comprise programming the programmable circuit with corresponding initial sets of variables comprising, for each measurement or transmission/reception operation of the sequence that permits obtaining the measurement: (1) which ones of the transducer elements of each of the assembled 616 phased arrays are to transmit and receive signals for each of the identified 604 acoustic measurements; (2) relative delays to be applied to each transducer element of the assembled 616 phased arrays for each of the identified 604 acoustic measurements; (3) gain and/or amplitude for each acoustic transducer element of each of the assembled 616 phased arrays; and (4) if applicable, timing to apply between different acoustic excitation signals for each of the identified 604 acoustic measurements; and (5) shape of the acoustic excitation signal that may have an influence on the frequency range of the acoustic excitation signal.

The method 600 may also comprise pre-calibrating 624 the configured 620 phased arrays. For example, the pre-calibration 624 may be performed to confirm proper functioning of the configured 620 phased arrays. The pre-calibration 624 may also or instead be utilized to initialize variables specific to the configured 620 phased arrays (e.g., corresponding to specific instances of the configured 620 phased arrays, such as may be identified by and/or otherwise associated with production serial numbers of the configured 620 phased arrays), such as initial relative gains to be applied to different transducer elements of the configured 620 phased arrays.

After the toolstring (comprising the configured 620 and perhaps pre-calibrated 624 phased arrays) is subsequently inserted 628 into the borehole, a first measurement may be performed 632 according to the measurement plan. The first measurement may be an auxiliary measurement to measure parameters that support subsequent ("second") measurements. After the first measurement, the phased arrays may be reconfigured. For example, one or more variables of the phased array module for subsequent measurements may be determined based on the first measurement, in particular the relative delays and gains of the transducer elements. The performed 632 measurements may include determining eccentricity of the toolstring within the borehole and/or wave propagation velocity in borehole fluid surrounding the phased arrays, among other examples.

The method 600 may also comprise performing an in-situ pre-calibration 636. That is, in contrast to the pre-calibration 624 performed before the toolstring is inserted 628 into the borehole, the in-situ pre-calibration 636 is performed while the toolstring is in the borehole. For example, the in-situ pre-calibration 636 may be utilized to re-determine (e.g., confirm and/or update) the variables assessed during the pre-calibration 624.

One or more second measurements may then be performed 640, herein referred to as main measurements. For example, for each main measurement, the FPGA of a phased array (or section thereof) serving as transmitter may send transmission commands to the transmitter components in the front-end electronics of the phased array, including the time delays corresponding to the operational mode of the main measurement(s) being performed 640. If the first measurement is an auxiliary measurement, the programmable circuit may take into account the result of the first measurement to adjust the variables of the phased array relative to the second measurement. The processing of the first measurement and adjusting of the variables of the phased array relative to second measurement may be performed downhole or at the surface. The receiving phased array(s), or the receiving section of the transmitter array in cases of pulse-echo type measurements, receives the pulse via the multi-channel receiver-components, after which the received pulse signals may be pre-treated (e.g., by the FPGA) as called for by the operational mode specified in the measurement plan.

The measurement plan may comprise more than one first measurement and/or more than one second (main) measurement. Where more than one main measurement is being performed 640, the main measurements may be performed 640 in parallel or sequentially. Each performed 640 measurement may take place in series or in parallel, applying predetermined parameters, such as signal shape (that may have an influence on the frequency range of the signal), time delays (including 0 or no delay) and gains (including 0, which indicates disabled) from a group of piezoelectric elements at controlled azimuthal positions of $\theta n$ (n=1, 2, 3, . . . , N), where $\theta n$ is the angle of borehole azimuth. The measurement may be in either or both transmission and reception, using respective sets of parameters to obtain the intended wavefront in different downhole environments.

As will be described below, the measurements are part of a looped sequence. After one or more measurements have been performed 640, the DSP (and/or FPGA(s)) associated with the phased arrays (such as described above with respect to FIGS. 3 and 4) may perform downhole processing 644 of the data obtained by the measurement(s) 640. Such downhole processing 644 may be utilized to, for example, reduce data size before the data is transmitted 648 uphole to surface equipment, and/or to extract information from the data on which subsequent decisions may be made, as described below. The downhole processing 644 may perform computations downhole, relative to the auxiliary measurements, for example, to determine one or more parameters of the wellbore or the tool, such as eccentricity or properties of the borehole fluid (wave propagation velocity in borehole fluid or acoustic impedance of the borehole fluid).

The data transmitted 648 to the surface equipment may be utilized to perform surface processing 660. For example, the real-time surface processing 660 may recuperate the data (e.g., to account for telemetry effects) and/or determine one or more answer products. The data and answer products determined by the surface processing 660 may be checked 664, whether manually by a person or automatically by software of the surface equipment. Such checking 664 may be utilized to judge the quality of the main measurement(s) 640.

A determination 668 may then be made regarding whether the measurement plan should be updated, such as based on the downhole processing 644 and/or the surface processing check 664. If the measurement plan does not need to be updated, then the toolstring is returned 676 to the surface, and final processing 680 may performed (e.g., via the surface equipment or otherwise), as described below, characterizing one or more of the formation, a casing disposed in the borehole, and/or an annulus between the casing and the formation, using results of the performed one or more acoustic measurements. Of course, characterization of the formation may be performed by the processor in the downhole tool and/or at the surface.

Updating the measurement plan may include repeating the same measurement(s) with one or more parameters of the main measurement(s) to be changed being updated 684. Such update 684 may include changing parameters of the performed main measurement(s) before the performed main measurement(s) is repeated. Updating the measurement plan may also comprise performing an additional measurement, which may also include changing the type of measurement (e.g., from pulse-echo to pitch-catch) or the operational mode (e.g., from unfocused mode to steering mode) of the measurement. In addition, the update 684 may be the result of a specific command from uphole instructions. After the update 684, delays and other processing parameters (e.g., driving sequence, timing, etc.) are applied 688 (e.g., phased arrays may be re-configured).

If additional measurements have been included in the measurement plan, the in-situ recalibration 652 may be performed. Thus, in-situ calibration may be continuously performed in the loop. The in-situ recalibration 652 may be utilized to alleviate the impact of sensor-related noise, among other examples. A dedicated operational mode of one or more of the phased arrays may be utilized for the in-situ recalibration 652. However, the in-situ recalibration 652 may instead (or also) be based on the data from the performed 640 main measurement(s), such as described in U.S. Pat. No. 10,114,138. The DSP and/or FPGA(s) associated with the phased arrays may be utilized to perform the calculations utilized for the in-situ recalibration 652.

In an example implementation within the scope of the present disclosure, the measurement plan may comprise a first measurement, in particular with the phased array configured to emit firing or acoustic excitation signals at a plurality of azimuths distributed all around the borehole simultaneously, such as with the phased array in flash mode, and at a relatively high logging speed. The measurement plan may be updated based on the result of the first measurement, in particular based on anomaly detected in the results of the first measurement for a particular zone of the borehole. In the specification, "anomaly" may comprise expected events such as top of cement, or casing thickness changes or unexpected events such as defective pipe or cement chanelling. For example, if a first type of anomaly is detected from the flash log, a first additional measurement may be triggered for the particular zone, and if a second anomaly is detected from the flash log, a second additional measurement may be triggered for the particular zone. Anomalies may include changes in measurements, such as amplitudes, their attenuations, phases, frequencies, delays and associated deliverables, that can be caused by defects in well structures such as casing, well cement and formation, and their geometries/relative positions and acoustic properties. When anomalies are detected and the first additional measurement is triggered, other acquisition parameters may be changed as well as part of the measurement plan update, such as the logging speed.

Updates may be controlled by the surface equipment or (e.g., if no surface communication is possible) an automatic fashion as pre-programmed in the phased arrays. User input and/or algorithms may be used for analyzing the processing and updating the measurement plan. Such updates may involve the re-application of delays and processing parameters 688, driving sequences, and/or timing between different main measurements.

Data obtained by performing 640 the main measurement (s) may be stored downhole, such as in memory available on one or multiple memory boards included in the different phased arrays and/or as a shared memory for different phased arrays. This data can be either the raw measurement data, data partially processed by the FPGA(s) of the phased array(s), and/or data partially processed by the DSP(s) and/or FPGA(s) associated with the phased arrays.

After the toolstring is returned 676 to surface, data from such memory can be read-out. This data may then be utilized by surface equipment (e.g., software operating on a processing system) for the final processing 680. Such processing 680 may be for final answer product generation, such as logs of corrosion and cement impedance for cased-hole implementations. In other implementations, all or part of the data may be sent uphole in real-time.

As described above, a measurement tool according to one or more aspects of the present disclosure may be configured to be able to provide several types of measurements. These measurements may be parameterizable in real-time while the tool is downhole.

Figure 57:
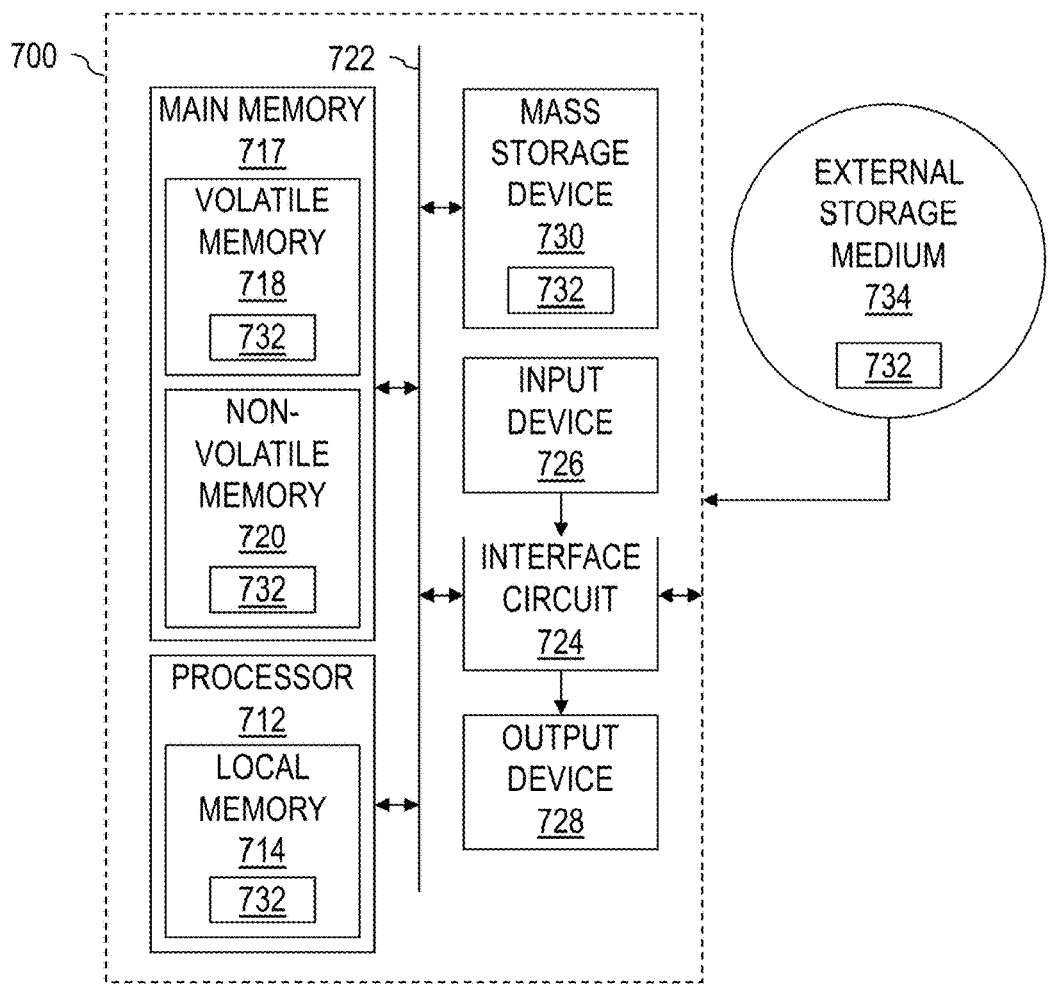
FIG. 57 is a schematic view of at least a portion of example implementation of a processing system according to one or more aspects of the present disclosure.

FIG. 57 is a schematic view of at least a portion of an example implementation of a processing system 700 according to one or more aspects of the present disclosure. The processing system 700 may execute machine-readable instructions to implement at least a portion of one or more of the methods and/or processes described herein, and/or to implement a portion of one or more of the example downhole tools and/or surface equipment described herein. The processing system 700 may be or comprise, for example, one or more processors, controllers, special-purpose computing devices, servers, personal computers, personal digital assistant (PDA) devices, smartphones, internet appliances, and/or other types of computing devices. The entirety of the processing system 700 may be implemented within downhole apparatus described above. One or more components or functions of the processing system 700 may also or instead be implemented in wellsite surface equipment, perhaps including the surface equipment 132 depicted in FIG. 1 and/or other surface equipment.

The processing system 700 may comprise a processor 712, such as a general-purpose programmable processor, among other examples. The processor 712 may comprise a local memory 714 and may execute program code instructions 732 present in the local memory 714 and/or another memory device. The processor 712 may execute, among other things, machine-readable instructions or programs to implement the methods and/or processes described herein. The programs stored in the local memory 714 may include program instructions or computer program code that, when executed by an associated processor, cause a controller and/or control system implemented in surface equipment and/or a downhole tool to perform tasks as described herein. The processor 712 may be, comprise, or be implemented by one or more processors of various types operable in the local application environment, and may include one or more general-purpose processors, special-purpose processors, microprocessors, DSPs, FPGAs, ASICs, processors based on a multi-core processor architecture, and/or other processors.

The processor 712 may be in communication with a main memory 717, such as via a bus 722 and/or other communication means. The main memory 717 may comprise a volatile memory 718 and a non-volatile memory 720. The volatile memory 718 may be, comprise, or be implemented by random access memory (RAM), static RAM (SRAM), dynamic RAM (DRAM), synchronous DRAM (SDRAM), RAMBUS DRAM (RDRAM), and/or other types of RAM devices. The non-volatile memory 720 may be, comprise, or be implemented by read-only memory, flash memory, and/or other types of memory devices. One or more memory controllers (not shown) may control access to the volatile memory 718 and/or the non-volatile memory 720.

The processing system 700 may also comprise an interface circuit 724. The interface circuit 724 may be, comprise, or be implemented by various types of standard interfaces, such as an Ethernet interface, a universal serial bus (USB), a wireless interface, and/or a cellular interface, among other examples. The interface circuit 724 may also comprise a graphics driver card. The interface circuit 724 may also comprise a communication device, such as a modem or network interface card, to facilitate exchange of data with external computing devices via a network, such as via Ethernet connection, digital subscriber line (DSL), telephone line, coaxial cable, cellular telephone system, and/or satellite, among other examples.

One or more input devices 726 may be connected to the interface circuit 724. One or more of the input devices 726 may permit a user to enter data and/or commands for utilization by the processor 712. Each input device 726 may be, comprise, or be implemented by a keyboard, a mouse, a touchscreen, a trackpad, a trackball, an image/code scanner, and/or a voice recognition system, among other examples.

One or more output devices 728 may also be connected to the interface circuit 724. One or more of the output devices 728 may be, comprise, or be implemented by a display device, such as a liquid crystal display (LCD), a light-emitting diode (LED) display, and/or a cathode ray tube (CRT) display, among other examples. One or more of the output devices 728 may also or instead be, comprise, or be implemented by a printer, speaker, and/or other examples.

The processing system 700 may also comprise a mass storage device 730 for storing machine-readable instructions and data. The mass storage device 730 may be connected to the interface circuit 724, such as via the bus 722. The mass storage device 730 may be or comprise a floppy disk drive, a hard disk drive, a compact disk (CD) drive, and/or digital versatile disk (DVD) drive, among other examples. The program code instructions 732 may be stored in the mass storage device 730, the volatile memory 718, the non-volatile memory 720, the local memory 714, and/or on a removable storage medium 734, such as a CD or DVD.

The mass storage device 730, the volatile memory 718, the non-volatile memory 720, the local memory 714, and/or the removable storage medium 734 may each be a tangible, non-transitory storage medium. The modules and/or other components of the processing system 700 may be implemented in accordance with hardware (such as in one or more integrated circuit chips, such as an ASIC), or may be implemented as software or firmware for execution by a processor. In the case of firmware or software, the implementation can be provided as a computer program product including a computer readable medium or storage structure containing computer program code (i.e., software or firmware) for execution by the processor.

Figure 58:
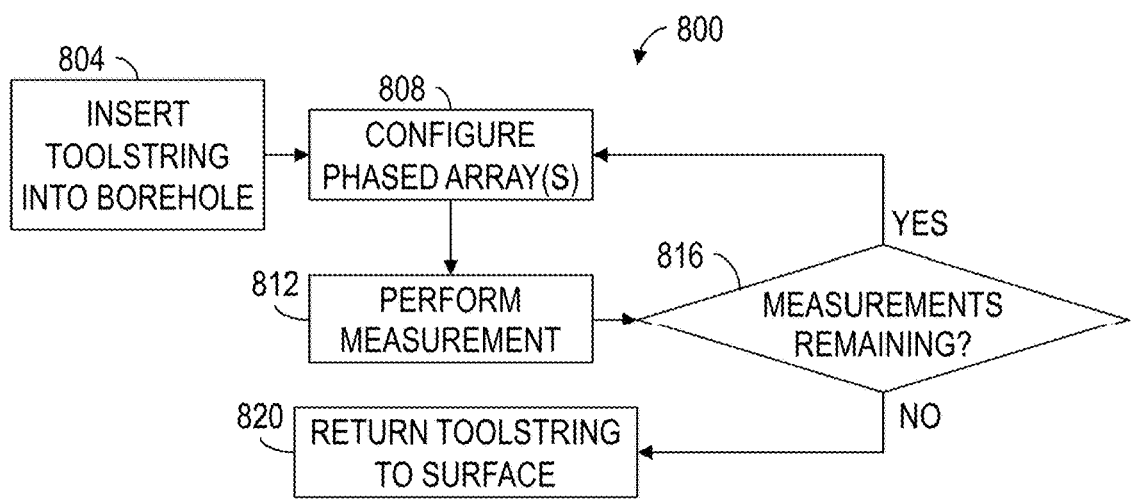
FIG. 58 is a flow-chart diagram of at least a portion of an example implementation of a method according to one or more aspects of the present disclosure.

FIG. 58 is a flow-chart diagram of at least a portion of an example implementation of a method 800 according to one or more aspects of the present disclosure. The method 800 is a simplified implementation of the example method 600 depicted in FIG. 56. Other implementations of the method 800 also within the scope of the present disclosure, however, may not include each aspect described below, and may also include aspects other than as described below, including aspects described above with respect to FIG. 56.

The method 800 comprises inserting 804 a toolstring into a borehole. The toolstring and borehole may be in accord with one or more aspects described above. Thereafter, while the toolstring is in the borehole, one or more phased arrays are configured 808 for acquisition by surface equipment, such as the surface equipment 132 depicted in FIG. 1. Such acquisition may be via various combinations described above, via one or more phased arrays implemented as described above. The configuration 808 may pertain to a planned or unplanned acoustic measurement via one or more transmissions/receptions in an operational mode, including the number and relative positions of one or more transmitter arrays and one or more receiver arrays (or transmitting/receiving elements of a single array), their respective firing and receiving modes, and their associated variable sets. Each associated variable set includes at least a number of elements and their positions (or indices), pulse shape representing frequency for transmission, relative time delays, and gain or amplitude control of each element. The acoustic measurement is then performed 812.

If additional measurements are determined 816 as remaining to be performed, the phased array(s) may be reconfigured 808 prior to performing 812 a subsequent measurement. If it is determined 816 that there are no remaining measurements to be performed, the toolstring is returned 820 to surface.

In view of the entirety of the present disclosure, including the figures and the claims, a person having ordinary skill in the art will readily recognize that the present disclosure introduces a method comprising: (A) determining a measurement plan comprising one or more acoustic measurements; (B) lowering in a borehole penetrating a subsurface formation a toolstring having one or more phased array modules, wherein each phased array module comprises: (i) a plurality of acoustic transducers operable to emit an acoustic excitation signal and receive an echo signal; and (ii) a programmable circuit configured to set one or more variables of the phased array modules; (C) configuring the one or more phased array modules, wherein configuring the one or more phased array modules includes programming the programmable circuit to set variables of the one or more phased array modules according to the measurement plan; (D) performing the one or more acoustic measurements of the measurement plan using the configured one or more phased array modules; and (E) characterizing one or more of the formation, a casing disposed in the borehole, and/or an annulus between the casing and the formation, using results of the performed one or more acoustic measurements.

The one or more variables may include at least one of: which ones of a plurality of transducer elements of the one or more phased array modules are to transmit and receive pulses; relative delays to be applied to each transducer element of the one or more phased array modules; and/or a gain control or amplitude control of each transducer element of the one or more phased array modules; and/or a shape of the acoustic excitation signal.

Each acoustic measurement may comprise a sequence of a plurality of transmission/reception operations, and configuring the phased array modules may comprise setting at least one of the variables before each of the transmission/reception operations.

The measurement plan may comprise a first acoustic measurement and a second acoustic measurement, the one or more phased array modules may comprise a plurality of phased array modules, and configuring the one or more phased array modules and performing the one or more acoustic measurements may comprise: configuring one of the phased array modules and performing the first acoustic measurement using that one of the phased array modules; and configuring a plurality of the phased array modules and performing the second acoustic measurement using those phased array modules.

A first one of the one or more acoustic measurements of the measurement plan may be obtainable via operation of one or more of the phased array modules in a first operational mode for generating a first wavefront having a first predetermined profile, a second one of the one or more acoustic measurements of the measurement plan may be obtainable via operation of one or more of the phased array modules in a second operational mode for generating a second wavefront having a second predetermined profile, and the first and second predetermined wavefront profiles may be different. One of the acoustic measurements may comprise a sequence of a plurality of transmission/reception operations, configuring the phased array modules may comprise setting at least one of the variables before each of the transmission/reception operations of the sequence, and the phased array modules may be configured such that each of the transmission/reception operations of the sequence are performed with the same number of transmitters and receivers and with the phased array modules operated in the same operational mode, wherein the transmitters and receivers may be selected so that a wavefront having a predetermined profile associated with the operational mode may be emitted toward a predetermined azimuth, and wherein the predetermined azimuths associated with each transmission/reception operation may be different. Relative delays to be applied to each transducer element of the phased array modules and/or a gain or amplitude control of each transducer element may be configured independently for each transmission/reception operation of the sequence.

Each acoustic measurement of the measurement plan may correspond to a measurement type selected from the group consisting of: a pulse-echo measurement in which an acoustic excitation signal is directed substantially normally to wall of the borehole; and a pitch-catch measurement in which an acoustic excitation signal is directed so as to reach the casing at a non-zero incidence angle relative to an axis normal to the borehole wall. The non-zero incidence angle may be defined in a longitudinal plane containing an axis of the borehole, or in an azimuthal plane normal to the borehole axis, so as to excite the casing along different directions. The non-zero incidence angle may be above or below a predetermined angle so as to excite different elastic modes in the casing, in particular relative to flexural, extensional, or thickness modes of the casing, toward desired directions.

The method may comprise updating the measurement plan based on results of a performed one or more of the acoustic measurements, wherein updating the measurement plan may include changing parameters of one of the acoustic measurements of the measurement plan and/or adding an additional acoustic measurement to the measurement plan. The measurement plan may be updated while the toolstring remains in the borehole. Configuring the one or more phased array modules may include programming the programmable circuit to set the variables according to the updated measurement plan and performing the one or more acoustic measurements of the updated measurement plan using the one or more phased array modules. The measurement plan may be updated based on results from processing of one of the performed acoustic measurements by a processor of the toolstring. The operation may further comprise: transmitting data based on one of the performed measurements to surface equipment disposed at a wellsite surface from whence the borehole originates; processing the transmitted data, via the surface equipment; and updating the measurement plan based on the data processed by the surface equipment.

The measurement plan may comprise at least one of: a main measurement for characterizing one or more of the formation, the casing, and/or the annulus; and an auxiliary measurement for characterizing the toolstring or an environment of the borehole surrounding the toolstring. The method may comprise performing the auxiliary measurement, configuring the phased array modules for the main measurement based on the results of the auxiliary measurement, and performing the main measurement. The method may comprise configuring the phased array modules for the main measurement based on the results of the auxiliary measurement, including setting variables corresponding to the relative delays and gain of each transducer element based on the results of the auxiliary measurement. The auxiliary measurement may be for characterizing at least one of: eccentering of the one or more phased arrays relative to a central axis of the borehole; and acoustic impedance and/or soundwave propagation speed of the fluid surrounding the toolstring in the borehole.

Each of the one or more acoustic measurements may relate to at least one of: measuring internal diameter of the borehole wall; determining thickness, surface geometry, and/or a corrosion indication of the casing; determining material state of the annulus; determining an acoustic property of the formation; and/or imaging formation texture and/or features, and for instance identifying a vug or fracture of the formation based on the image. Performing the one or more acoustic measurements may comprise performing a first one of the one or more acoustic measurements while the toolstring is moved in a first trip through a first portion of the borehole. The method may comprise updating the measurement plan by processing results of the first acoustic measurement and changing parameters of one of the acoustic measurements of the measurement plan and/or adding an acoustic measurement to the measurement plan. The method may also comprise performing a second acoustic measurement while the toolstring is moved in a second trip through a second portion of the borehole, wherein the second acoustic measurement may be the changed and/or added acoustic measurement, and wherein the first portion of the borehole may comprise the second portion of the borehole. The method may further comprise detecting an anomaly in the results of the first acoustic measurement in the second portion of the borehole. The method may further comprise identifying a type of the anomaly and selecting the second measurement based on the type of the identified anomaly. A phased array module utilized for the first acoustic measurement may be configured to emit acoustic excitation signals simultaneously at a plurality of azimuths distributed fully around the borehole. In a particular embodiment, the phased array module utilized for the first acoustic measurement is configured to emit acoustic excitation signals simultaneously at a first plurality of azimuths distributed fully around the borehole and receiving excitation signals simultaneously at a second plurality of azimuths distributed fully around the borehole. The first and second plurality of azimuths may be the same or different.

The present disclosure also introduces a system comprising: (A) a toolstring comprising one or more phased array modules and configurable for operation in a borehole that extends into a subsurface formation, wherein each phased array module comprises: (i) a plurality of acoustic transducer elements operable to emit an acoustic excitation signal and receive an echo signal; and (ii) a programmable circuit operable to set one or more variables relative to the one or more phased array modules, wherein the toolstring is configurable to perform a plurality of measurements using the one or more phased array modules, each measurement corresponding to a different configuration by the programmable circuit of each phased array module; and (B) a processing system configured to characterize one or more of the formation, a casing disposed in the borehole, and/or an annulus between the casing and the formation, using at least one measurement obtained via operation of one or more of the one or more phased array modules.

The variables may comprise at least one of: which ones of a plurality of transducer elements of one or more of the phased array modules are to transmit and/or receive pulses; relative delays to be applied to each transducer element; gain and/or amplitude control of each transducer element; and a shape of the acoustic excitation signal. The toolstring may comprise a plurality of phased array modules, wherein each of the phased array modules may be substantially similar in structure. The transducer elements of one or more phased array modules may be arranged in a 2D matrix having multiple, circumferentially extending rows, and/or in a 1D matrix having a single, circumferentially extending row.

Each of the one or more phased array modules may include: at least one transmitter component for emitting the acoustic excitation signal; and at least one reception component for recording the received echo signal. Each programmable circuit may includes: a plurality of transducer connection means for selectively connecting the transmitter and reception components to corresponding ones of the transducer elements; and a control unit connected to each of the transmitter and reception components and the plurality of transducer connection means, wherein the control unit may control operation of each of the transmitter and reception components and the transmitter connection means. The one or more phased array modules may include: a DSP connected to the FPGA and comprising a DAC; a controller board; a memory board connected to the DSP and the controller board; and a power supply board connected to and providing electrical power to the memory and controller boards.

The present disclosure also introduces a method comprising causing operation of one or more phased arrays of acoustic transducers of a toolstring in a borehole penetrating a subterranean formation, wherein the operation comprises: performing one or more acoustic measurements of a predetermined measurement plan, wherein the predetermined measurement plan comprises a plurality of different types of acoustic measurements via different corresponding operation of one or more of the phased arrays; then while the toolstring remains in the borehole, changing parameters of a performed one of the acoustic measurements, an unperformed one of the acoustic measurements, or a calibration of the phased arrays, based on one of the performed acoustic measurements; and then performing an unperformed one or more of the acoustic measurements or reperforming a performed one of the acoustic measurements.

Changing the parameters of the performed or unperformed one of the acoustic measurements may be based on results from processing of one of the performed acoustic measurements by a processor of the toolstring.

The operation may further comprise transmitting data based on one of the performed measurements to surface equipment disposed at a wellsite surface from whence the borehole originates. Changing the parameters of the performed or unperformed one of the acoustic measurements may be based on results from processing of the transmitted data by the surface equipment.

The plurality of different types of acoustic measurements may include: different types of main measurements each characterizing one or more of the formation, the borehole, cement securing a casing in the borehole, and/or the casing; and different types of auxiliary measurements each utilized to adjust parameters of one or more of the main measurements. The main measurements may include at least two of: a measurement based on time-based pulse-echo operation of at least one of the phased arrays; a measurement based on frequency-based pulse-echo operation of at least one of the phased arrays; a measurement based on flexural-mode pitch-catch operation of at least two of the phased arrays; a measurement based on extension-mode pitch-catch operation of at least two of the phased arrays; a measurement based on omnidirectional operation of at least one of the phased arrays; and a measurement based on a combination of pulse-echo and pitch-catch operation of at least two of the phased arrays. One of the auxiliary measurements may characterize eccentering of the phased arrays relative to an axial centerline of the borehole. One of the auxiliary measurements may characterize acoustic wave propagation velocity in borehole fluid surrounding the phased arrays. The operation may further comprise, after each main measurement is performed: processing the main measurement by a processor of the toolstring to generate a reduced-size data set; and transmitting the reduced-size data set to surface equipment disposed at a wellsite surface from whence the borehole originates. The operation may further comprise, after each main measurement is performed, processing the main measurement by a processor of the toolstring to extract information. The changed parameters may be changed based on the extracted information. The operation may further comprise, after each of one or more of the main measurements is performed, determining that downhole condition changes are sufficient to reperform one or more outdated ones of the auxiliary measurements, and reperforming the one or more outdated auxiliary measurements. The downhole condition changes may include one or more of: one or more characteristics of borehole fluid surrounding the phased arrays, wherein the one or more characteristics is one or more of pressure, temperature, density, viscosity, flow rate, and propagation velocity; and positioning of the phased arrays within the borehole.

The operation may further comprise performing a calibration of the phased arrays in the borehole prior to performing the acoustic measurements. The calibration may adjust variables specific to the phased arrays. The calibrated variables may include relative gains between different elements of the phased arrays.

The method may further comprise, before causing operation of the phased arrays: determining a minimum number of the phased arrays to include in the toolstring that is sufficient to obtain each of the plurality of different types of acoustic measurements of the predetermined measurement plan without removing the toolstring from the borehole; assembling the toolstring with the determined number of phased arrays; configuring the assembled phased arrays according to the predetermined measurement plan; and performing a pre-calibration of the configured phased arrays. Each of the phased arrays may be substantially similar in structure. Each phased array may comprise: (A) a plurality of transducer elements each comprising a piezoelectric element; and (B) acquisition electronics comprising: (i) a plurality of transducer connection means for selectively connecting to corresponding ones of the transducer elements; (ii) a plurality of transmitter components each corresponding to one of the transducer elements; (iii) a plurality of reception components each corresponding to one of the transducer elements; (iv) a plurality of TX/RX switches each corresponding to one of the transducer elements and operable to selectively connect a corresponding one of the transducer connection means with a corresponding one of the transmitter components and a corresponding one of the reception components; (v) an FPGA connected to each of the transmitter components and each of the reception components; (vi) a DSP connected to the FPGA and comprising a DAC; (vii) a controller board; (viii) a memory board connected to the DSP and the controller board; and (ix) a power supply board connected to and providing electrical power to the memory and controller boards. The piezoelectric elements may be arranged in a 2D matrix having multiple, circumferentially extending rows. The piezoelectric elements may be arranged in a 1D matrix having a single, circumferentially extending row. Each piezoelectric element may be substantially rectangular and may have a major axis extending parallel to a central axis of the toolstring. Each piezoelectric element may be substantially square. The piezoelectric elements may be arranged as a paved array. The piezoelectric elements may be arranged in an arbitrary configuration.

The present disclosure also introduces a method comprising: (A) for a toolstring to be operated in a borehole penetrating a subterranean formation, determining a number of phased arrays of acoustic transducers to include in the toolstring that is sufficient to obtain a predetermined plurality of acoustic imaging measurements via operation of the toolstring without removing the toolstring from the borehole; (B) assembling the toolstring with the determined number of phased arrays; (C) configuring the assembled phased arrays according to the predetermined plurality of acoustic imaging measurements; (D) inserting the toolstring in the borehole; and (E) without removing the toolstring from the borehole: (i) operating the phased arrays to obtain one of the predetermined acoustic imaging measurements; and (ii) operating the phased arrays to obtain an additional acoustic imaging measurement not included in the predetermined plurality of acoustic imaging measurements.

A first one of the predetermined acoustic imaging measurements may be obtainable via operation of one or more of the assembled phased arrays in a first operational mode, a second one of the predetermined acoustic imaging measurements may be obtainable via operation of one or more of the assembled phased arrays in a second operational mode, the additional acoustic imaging measurement not included in the predetermined plurality of acoustic imaging measurements may be obtainable via operation of one or more of the assembled phased arrays in a third operational mode, and the first, second, and third operational modes may be different. The first, second, and third operational modes may be different ones selected from the group consisting of: an eccentricity determination mode; an axially focused mode; an axially unfocused mode; an azimuthal steering mode; a flash mode; a separated firing/reception mode; an axially directed mode with incidence below a predetermined angle; an axially directed mode with incidence above the predetermined angle; an omnidirectional mode; and a calibration mode.

A first one of the predetermined acoustic imaging measurements may be a first measurement type, a second one of the predetermined acoustic imaging measurements may be a second measurement type, the additional acoustic imaging measurement not included in the predetermined plurality of acoustic imaging measurements may be a third measurement type, and the first, second, and third measurement types may be different. The first, second, and third measurement types may be different ones selected from the group consisting of: a time-based, pulse-echo measurement; a frequency-based, pulse-echo measurement; a flexural pitch-catch measurement; an extensional pitch-catch measurement; an omnidirectional pitch-catch measurement; and a combination pule-echo, pitch-catch measurement.

The predetermined acoustic imaging measurements and the additional acoustic imaging measurement may each be characterized by a corresponding combination of: one of a plurality of different measurement types; and operation of one or more of the assembled phased arrays in one of a plurality of different operational modes. The combination characterizing the additional acoustic imaging measurement may be different from each combination characterizing the predetermined acoustic imaging measurements. The combination characterizing a first one of the predetermined acoustic imaging measurements may be different than the combination characterizing a second one of the predetermined acoustic imaging measurements. Each operational mode may be selected from the group consisting of an eccentricity determination mode, an axially focused mode, an axially unfocused mode, an azimuthal steering mode, a flash mode, a separated firing/reception mode, an axially directed mode with incidence below a predetermined angle, an axially directed mode with incidence above the predetermined angle, an omnidirectional mode, and a calibration mode, and each measurement type may be selected from the group consisting of a time-based, pulse-echo measurement, a frequency-based, pulse-echo measurement, a flexural pitch-catch measurement, an extensional pitch-catch measurement, an omnidirectional pitch-catch measurement, and a combination pule-echo, pitch-catch measurement.

Operating the phased arrays to obtain the one of the predetermined acoustic imaging measurements may comprise operating the phased arrays while the toolstring is moved uphole in a first trip through a first portion of the borehole, and operating the phased arrays to obtain the additional acoustic imaging measurement may comprise operating the phased arrays while the toolstring is moved uphole in a second trip through a second portion of the borehole, wherein the first portion of the borehole may comprise the second portion of the borehole. The method may further comprise identifying the second portion of the borehole based on the obtained one of the predetermined acoustic imaging measurements.

Determining the number may comprise determining a minimum number of the phased arrays to include in the toolstring that is sufficient to obtain the predetermined plurality of acoustic imaging measurements via operation of the toolstring without removing the toolstring from the borehole. The predetermined plurality of acoustic imaging measurements may comprise: a compensated flexural measurement using an axially high-angle incident emitted wavefront; and two frequency-based pulse-echo measurements made at different axial positions. The determined minimum number of phased arrays may be four phased arrays, and operating the configured phased arrays in the borehole may comprise: obtaining the compensated flexural measurement by operating the configured phased arrays in a TX-RX-RX-TX arrangement in which an uppermost one of the phased arrays is operated as a transmitter (TX), a lowermost one of the phased arrays is operated as a TX, and two phased arrays disposed between the uppermost and lowermost phased arrays are each operated as a receiver (RX); and obtaining each of the pulse-echo measurements, each by operating two of the phased arrays when those two phased arrays are not being operated to obtain the compensated flexural measurement.

Determining the number may comprise determining a maximum number of the phased arrays to include in the toolstring that is sufficient to obtain the predetermined plurality of acoustic imaging measurements via operation of the toolstring without removing the toolstring from the borehole. The predetermined plurality of acoustic imaging measurements may comprise: a compensated flexural measurement using an axially high-angle incident emitted waveform; and two frequency-based pulse-echo measurements made at different axial positions. The determined maximum number of phased arrays may be 2+N phased arrays, wherein N is an integer not less than 2, and operating the configured phased arrays in the borehole may comprise: obtaining the compensated flexural measurement by operating the configured phased arrays in a TX-N(RX)-TX arrangement in which an uppermost one of the phased arrays is operated as a transmitter (TX), a lowermost one of the phased arrays is operated as a TX, and N phased arrays disposed between the uppermost and lowermost phased arrays are each operated as a receiver (RX); and obtaining each of the pulse-echo measurements, each by operating two of the phased arrays not utilized to obtain the compensated flexural measurement.

The predetermined plurality of acoustic imaging measurements may comprise: a quick-log, non-compensated, extensional measurement using a flash-mode; and a high-resolution, pulse-echo measurement of a section identified during the quick-log. The determined number of phased arrays may be three phased arrays. Operating the configured phased arrays in the borehole may comprise: obtaining the quick-log, non-compensated, extensional measurement by operating the configured phased arrays in a TX-RX-RX arrangement, in which an uppermost one of the phased arrays is operated as a transmitter (TX) and the two other phased arrays are each operated as a receiver (RX), while the toolstring is moved uphole in a first trip through a predetermined portion of the borehole; and obtaining the pulse echo-measurement by operating one of the phased arrays while the toolstring is moved uphole in a second trip through the predetermined portion of the borehole.

Configuring the assembled phased arrays according to the predetermined plurality of acoustic imaging measurements may comprise: (A) connecting the assembled phased arrays to a processing system operable to execute operating software that contains a measurement plan describing the predetermined plurality of acoustic imaging measurements; and (B) commencing operation of the processing system, whereby the operating software communicates the measurement plan to the assembled phased arrays and selects: (i) corresponding modes in which firmware and acquisition electronics associated with the assembled phased arrays are to function to obtain the predetermined plurality of acoustic imaging measurements; and (ii) relative timing of the predetermined plurality of acoustic imaging measurements.

The present disclosure also introduces a method comprising causing operation of a number of phased arrays of acoustic transducers of a toolstring in a borehole penetrating a subterranean formation, wherein the operation comprises: (A) performing one or more acoustic measurements of a predetermined measurement plan, wherein the predetermined measurement plan comprises a plurality of different types of acoustic measurements via different corresponding operation of one or more of the phased arrays; and then (B) while the toolstring remains in the borehole: changing parameters of a performed or unperformed one of the acoustic measurements based on one of the performed acoustic measurements; then recalibrating the phased arrays; and then performing or reperforming the changed one of the unperformed or performed acoustic measurements.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method comprising:
    determining a measurement plan comprising one or more acoustic measurements;
    lowering, in a borehole penetrating a subsurface formation, a toolstring having one or more phased array modules, wherein each phased array module comprises:
        a plurality of acoustic transducers operable to emit an acoustic excitation signal and receive an echo signal; and
        a programmable circuit configured to set one or more variables of the phased array modules;
    configuring, while the toolstring is in the borehole, at least one of the one or more phased array modules by programming the programmable circuit to set variables of the configured one or more phased array modules according to the measurement plan;
    performing the one or more acoustic measurements of the measurement plan using the configured one or more phased array modules; and
    characterizing one or more of the formation, a casing disposed in the borehole, and/or an annulus between the casing and the formation, using results of the performed one or more acoustic measurements.

2. A method according to claim 1 wherein the one or more variables include at least one of:
    which ones of a plurality of transducer elements of the one or more phased array modules are to transmit and receive pulses;
    relative delays to be applied to each transducer element of the one or more phased array modules; and
    a gain control or amplitude control of each transducer element of the one or more phased array modules,
    a shape of the acoustic excitation signal,
    a frequency.

3. A method according to claim 1 wherein:
    a first one of the one or more acoustic measurements of the measurement plan is obtainable via operation of one or more of the phased array modules in a first operational mode for generating a first wavefront having a first predetermined profile;
    a second one of the one or more acoustic measurements of the measurement plan is obtainable via operation of one or more of the phased array modules in a second operational mode for generating a second wavefront having a second predetermined profile; and
    the first and second predetermined wavefront profiles are different.

4. A method according to claim 3 wherein:
    one of the acoustic measurements comprises a sequence of a plurality of transmission/reception operations;
    configuring the phased array modules comprises setting at least one of the variables before each of the transmission/reception operations of the sequence; and
    the phased array modules are configured such that each of the transmission/reception operations of the sequence are performed with the same number of transmitters and receivers and with the phased array modules operated in the same operational mode, the transmitters and receivers being selected so that a wavefront having a predetermined profile associated to the operational mode is emitted toward a predetermined azimuth, and the predetermined azimuths associated with each transmission/reception operation are different.

5. A method according to claim 3, wherein the first operational mode is selected so that the wavefront is a focused wavefront, wherein the first operational mode is used for imaging a surface of the casing, and
    wherein the second operational mode is selected so that the wavefront is an unfocused wavefront, wherein the second operational mode is used for characterizing at least one of the annulus between the casing and the formation and casing thickness.

6. The method according to claim 5, wherein the phased array module is configured in the second operational mode so that frequency bandwidth of the wavefront includes a casing resonance frequency.

7. A method according to claim 1 further comprising updating the measurement plan based on results of a performed one or more of the acoustic measurements, wherein updating the measurement plan includes reconfiguring at least one of the one or more phased array modules, changing parameters of one of the acoustic measurements of the measurement plan and/or adding an additional acoustic measurement to the measurement plan.

8. A method according to claim 1 wherein the measurement plan comprises at least one of:
a main measurement for characterizing one or more of the subsurface formation, the casing, and/or the annulus; and
an auxiliary measurement for characterizing the toolstring or an environment of the borehole surrounding the toolstring.

9. A method according to claim 8 wherein the auxiliary measurement is for characterizing at least one of:
eccentering of the one or more phased arrays relative to a central axis of the borehole; and
acoustic impedance and/or soundwave propagation speed of the fluid surrounding the toolstring in the borehole.

10. A method according to claim 1 wherein each of the one or more acoustic measurements relate to at least one of:
measuring internal diameter of the borehole wall;
determining thickness, surface geometry, and/or a corrosion indication of the casing;
determining material state of the annulus;
determining an acoustic property of the formation; or
imaging a formation texture and/or feature.

11. A method according to claim 1 wherein:
performing the one or more acoustic measurements comprises performing a first one of the one or more acoustic measurements while the toolstring is moved in a first trip through a first portion of the borehole;
the method comprises updating the measurement plan by:
  processing results of the first acoustic measurement; and
  reconfiguring, while the toolstring remains in the borehole, at least one of the one or more phased array modules, hanging parameters of one of the acoustic measurements of the measurement plan and/or adding an acoustic measurement to the measurement plan; and
performing a second acoustic measurement while the toolstring is moved in a second trip through a second portion of the borehole, wherein the second acoustic measurement is the changed and/or added acoustic measurement, and wherein the first portion of the borehole comprises at least a part of the second portion of the borehole.

12. A method according to claim 11 further comprising detecting an anomaly in the results of the first acoustic measurement in the second portion of the borehole and updating the measurement plan based on the anomaly detection.

13. A method according to claim 11 wherein a phased array module utilized for the first acoustic measurement is configured to emit acoustic excitation signals simultaneously at a first plurality of azimuths distributed fully around the borehole and receiving excitation signals simultaneously at a second plurality of azimuths distributed fully around the borehole.

14. A method according to claim 11, comprising, processing the main measurement by a processor of the toolstring to extract information, wherein changing parameters of one of the acoustic measurements of the measurement plan and/or adding an acoustic measurement to the measurement plan is performed based on the extracted information.

15. A method according to claim 11, comprising transmitting data based on one of the performed measurements to surface equipment disposed at a wellsite surface from whence the borehole originates, wherein changing the parameters of the one of the acoustic measurements of the measurement plan and/or adding an acoustic measurement to the measurement plan is based on results from processing of the transmitted data by the surface equipment.

16. A method according to claim 11 wherein updating the measurement plan further comprises changing one or more additional acquisition parameter, wherein the one or more acquisition parameters includes at least a logging speed of the toolstring.

17. A method according to claim 11, wherein changing parameters of one of the acoustic measurements of the measurement plan and/or adding an acoustic measurement to the measurement plan is performed while the toolstring remains in the borehole.

18. A system comprising:
a toolstring comprising one or more phased array modules and configurable for operation in a borehole that extends into a subsurface formation, wherein each phased array module comprises:
  a plurality of acoustic transducer elements operable to emit an acoustic excitation signal and receive an echo signal; and
  a programmable circuit operable to set one or more variables relative to at least one of the one or more phased array modules, wherein the toolstring is configurable to perform a plurality of measurements using the one or more phased array modules, each measurement corresponding to a different configuration by the programmable circuit of each phased array module, wherein the phased array modules are reconfigurable while the toolstring is disposed in the borehole after performing an initial measurement in the borehole; and
a processing system configured to characterize one or more of the formation, a casing disposed in the borehole, and/or an annulus between the casing and the formation, using at least one measurement obtained via operation of one or more of the one or more phased array modules.

19. A system according to claim 18 wherein the variables comprise at least one of:
which ones of a plurality of transducer elements of one or more of the phased array modules are to transmit and/or receive pulses;
relative delays to be applied to each transducer element;
gain and/or amplitude control of each transducer element
a shape of the acoustic excitation signal; and
a frequency.

20. A system according to claim 18 wherein:
each of the one or more phased array modules includes:
  at least one transmitter component for emitting the acoustic excitation signal; and
  at least one reception component for recording the received echo signal; and
each programmable circuit includes:
  a plurality of transducer connection means for selectively connecting the transmitter and reception components to corresponding ones of the transducer elements; and
  a control unit connected to each of the transmitter and reception components and the plurality of transducer connection means, wherein the control unit controls operation of each of the transmitter and reception components and the transmitter connection means.

* * * * *